United States Patent
Cao et al.

(10) Patent No.: US 12,274,888 B2
(45) Date of Patent: Apr. 15, 2025

(54) CARDIAC ELECTRICAL SIGNAL MORPHOLOGY AND PATTERN-BASED T-WAVE OVERSENSING REJECTION

(71) Applicant: Medtronic, Inc., Minneapolis, MN (US)

(72) Inventors: Jian Cao, San Jose, CA (US); Saul E. Greenhut, Parker, CO (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 181 days.

(21) Appl. No.: 18/311,861

(22) Filed: May 3, 2023

(65) Prior Publication Data
US 2023/0264035 A1    Aug. 24, 2023

Related U.S. Application Data

(63) Continuation of application No. 17/105,787, filed on Nov. 27, 2020, now Pat. No. 11,654,291, which is a
(Continued)

(51) Int. Cl.
*A61B 5/0464*    (2006.01)
*A61B 5/00*    (2006.01)
(Continued)

(52) U.S. Cl.
CPC ............ *A61N 1/3956* (2013.01); *A61B 5/283* (2021.01); *A61B 5/316* (2021.01); *A61B 5/341* (2021.01);
(Continued)

(58) Field of Classification Search
CPC ...... A61N 1/362; A61N 1/3621; A61N 1/365; A61N 1/36507; A61N 1/39; A61N 1/3956;
(Continued)

(56) References Cited

U.S. PATENT DOCUMENTS

| | | |
|---|---|---|
| 5,354,316 A | 10/1994 | Keimel |
| 5,545,186 A | 8/1996 | Olson et al. |

(Continued)

FOREIGN PATENT DOCUMENTS

| | | |
|---|---|---|
| EP | 2014228 A1 | 1/2009 |
| WO | 2006105391 A1 | 10/2006 |

OTHER PUBLICATIONS

First Office Action for CN Application No. 201780046415.4 dated Feb. 17, 2023, 17 pages.
(Continued)

*Primary Examiner* — Eugene T Wu

(57) ABSTRACT

A medical device, such as an extra-cardiovascular implantable cardioverter defibrillator (ICD), senses R-waves from a first cardiac electrical signal by a first sensing channel and stores a time segment of a second cardiac electrical signal acquired by a second sensing channel in response to each sensed R-wave. The ICD determines morphology match scores from the stored time segments of the second cardiac electrical signal and, based on the morphology match scores, withholds detection of a tachyarrhythmia episode. In some examples, the ICD detects T-wave oversensing based on the morphology match scores and withholds detection of a tachyarrhythmia episode in response to detecting the T-wave oversensing.

22 Claims, 18 Drawing Sheets

Related U.S. Application Data continuation of application No. 15/655,082, filed on Jul. 20, 2017, now Pat. No. 10,850,113.

(60) Provisional application No. 62/367,221, filed on Jul. 27, 2016.

(51) Int. Cl.
| | |
|---|---|
| *A61B 5/283* | (2021.01) |
| *A61B 5/316* | (2021.01) |
| *A61B 5/341* | (2021.01) |
| *A61B 5/349* | (2021.01) |
| *A61B 5/35* | (2021.01) |
| *A61B 5/352* | (2021.01) |
| *A61B 5/363* | (2021.01) |
| *A61N 1/39* | (2006.01) |
| *A61B 5/364* | (2021.01) |

(52) U.S. Cl.
CPC ............... *A61B 5/349* (2021.01); *A61B 5/35* (2021.01); *A61B 5/352* (2021.01); *A61B 5/363* (2021.01); *A61B 5/4836* (2013.01); *A61B 5/686* (2013.01); *A61B 5/7221* (2013.01); *A61N 1/3925* (2013.01); *A61N 1/3987* (2013.01); *A61B 5/364* (2021.01)

(58) Field of Classification Search
CPC .............. A61N 1/3987; A61B 5/04012; A61B 5/0452; A61B 5/04525; A61B 5/0456; A61B 5/046; A61B 5/0464; A61B 5/72; A61B 5/7203; A61B 5/7221; A61B 5/7235; A61B 5/7239; A61B 5/7246; A61B 5/7253; A61B 5/726; A61B 5/7264; A61B 5/7282

See application file for complete search history.

(56) References Cited

U.S. PATENT DOCUMENTS

| | | | |
|---|---|---|---|
| 6,393,316 | B1 | 5/2002 | Gillberg et al. |
| 7,031,765 | B2 | 4/2006 | Ritscher et al. |
| 7,031,771 | B2 | 4/2006 | Brown et al. |
| 7,330,757 | B2 | 2/2008 | Ostroff et al. |
| 7,444,182 | B2 | 10/2008 | Ostroff et al. |
| 7,515,956 | B2 | 4/2009 | Thompson |
| 7,627,368 | B2 | 12/2009 | Houben et al. |
| 7,734,333 | B2 | 6/2010 | Ghanem et al. |
| 7,734,336 | B2 | 6/2010 | Ghanem et al. |
| 7,761,150 | B2 | 7/2010 | Ghanem et al. |
| 7,769,452 | B2 | 8/2010 | Ghanem et al. |
| 7,831,304 | B2 | 11/2010 | Cao et al. |
| 7,907,993 | B2 | 3/2011 | Ghanem et al. |
| 7,941,214 | B2 | 5/2011 | Kleckner et al. |
| 7,991,471 | B2 | 8/2011 | Ghanem et al. |
| 8,050,754 | B2 | 11/2011 | Ostroff et al. |
| 8,095,206 | B2 | 1/2012 | Ghanem et al. |
| 8,160,684 | B2 | 4/2012 | Ghanem et al. |
| 8,306,618 | B2 | 11/2012 | Ghanem et al. |
| 8,435,185 | B2 | 5/2013 | Ghanem et al. |
| 8,437,842 | B2 | 5/2013 | Zhang et al. |
| 8,825,145 | B1 | 9/2014 | Zhang |
| 8,886,296 | B2 | 11/2014 | Patel |
| 8,914,106 | B2 | 12/2014 | Charlton et al. |
| 8,942,802 | B2 | 1/2015 | Ostroff et al. |
| 8,977,350 | B2 | 3/2015 | Sarkar et al. |
| 8,983,586 | B2 | 3/2015 | Zhang |
| 10,252,071 | B2 | 4/2019 | Cao et al. |
| 2003/0204215 | A1 | 10/2003 | Gunderson et al. |
| 2004/0015197 | A1 | 1/2004 | Gunderson |
| 2004/0111120 | A1 | 6/2004 | Sarkar et al. |
| 2004/0230233 | A1 | 11/2004 | Gunderson et al. |
| 2006/0224075 | A1 | 10/2006 | Gunderson et al. |
| 2006/0235476 | A1 | 10/2006 | Gunderson et al. |
| 2007/0232948 | A1 | 10/2007 | Stadler et al. |
| 2008/0082014 | A1 | 4/2008 | Cao et al. |
| 2008/0275516 | A1 | 11/2008 | Ghanem et al. |
| 2010/0185111 | A1 | 7/2010 | Miller |
| 2011/0270102 | A1 | 11/2011 | Zhang et al. |
| 2011/0270109 | A1 | 11/2011 | Zhang et al. |
| 2014/0277221 | A1 | 9/2014 | Charlton et al. |
| 2015/0306375 | A1 | 10/2015 | Marshall et al. |
| 2015/0306410 | A1 | 10/2015 | Marshall et al. |
| 2016/0022166 | A1 | 1/2016 | Stadler et al. |
| 2016/0022999 | A1 | 1/2016 | Zhang et al. |
| 2016/0023013 | A1 | 1/2016 | Greenhut et al. |
| 2016/0113536 | A1 | 4/2016 | Greenhut et al. |
| 2016/0158567 | A1 | 6/2016 | Marshall et al. |
| 2016/0235315 | A1 | 8/2016 | Sarkar et al. |
| 2016/0235320 | A1 | 8/2016 | Sarkar et al. |
| 2016/0235321 | A1 | 8/2016 | Sarkar et al. |
| 2016/0235992 | A1 | 8/2016 | Sarkar et al. |
| 2017/0312532 | A1* | 11/2017 | Zhang ..................... A61B 5/29 |

OTHER PUBLICATIONS

Weiss et al., "Safety and Efficacy of a Totally Subcutaneos Implantable-Cardioverter Defibrillator", Circulation, vol. 128, 2013, 11 pages.

Burke et al., "Safety and Efficacy of the Totally Subcutaneous Implantable Defibrillator 2-Year Results From a Pooled Analysis of the IDE Study and Effortless Registry", Journal of the American College of Cardiology, vol. 65, No. 16, 2015 11 pages.

Lambiase et al., "Worldwide experience with a totally subcutaneous implantable defibrillator: early results from the Effortless S-ICD Registry", European Heart Journal Advance Access published Mar. 26, 2014, 10 pages.

Kooiman et al., "Inappropriate subcutaneous implantable cardioverter defibrillator shocks due to T-Wave oversensing can be prevented. Implications for management", Heart Rhythm, 2013, 31 pages.

Brisben et al., "A New Algorithm to Reduce Inappropriate Therapy in the S-ICD System" Journal of Cardiovascular Electrophysiology, 2015, vol. 26,19 pages.

Cao et al., "A fully automatic, implantable cardioverter-defibrillator algorithm to prevent inappropriate detection of ventricular tachycardia or fibrillation due to T-wave oversensing in spontaneous rhythm", Hearth Rhythm, 2012, vol. 9, 9 pages.

Brown et al., "PainFreeSST Trial: T-wave OversensingAlgorithm Performance", Electrophysiology Society Conference 2015, Poster. (PCT/US2017/043823) PCT Notification of Transmittal of the International Search Report and the Written Opinion of the International Searching Authority, dated Oct. 26, 2017, 13 pages.

\* cited by examiner

CARDIAC ELECTRICAL SIGNAL MORPHOLOGY AND PATTERN-BASED T-WAVE OVERSENSING REJECTION

REFERENCE TO RELATED APPLICATIONS

This application is a continuation of U.S. application Ser. No. 17/105,787, filed on Nov. 27, 2020, which is a continuation of U.S. application Ser. No. 15/655,082, filed on Jul. 20, 2017, granted as U.S. Pat. No. 10,850,113, which claims the benefit of provisional U.S. patent application Ser. No. 62/367,221, filed on Jul. 27, 2016, the content of all of which incorporated herein by reference in its entirety.

TECHNICAL FIELD

The disclosure relates generally to a medical device system and method for rejecting T-wave oversensing (TWOS) based on cardiac electrical signal morphology and cardiac event patterns.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for detecting T-wave oversensing (TWOS) and rejecting a ventricular tachyarrhythmia detection in response to detecting TWOS. A medical device system, such as an extracardiovascular ICD system, operating according to the techniques disclosed herein may determine morphology match scores of cardiac electrical signal segments corresponding to consecutively sensed events for identifying TWOS based on the morphology match scores.

In one example, the disclosure provides an extra-cardiovascular ICD system including a sensing circuit, a memory, and a control circuit. The sensing circuit includes a first sensing channel configured to receive a first cardiac electrical signal via a first extra-cardiovascular sensing electrode vector coupled to the extra-cardiovascular ICD. The first sensing channel is configured to sense R-waves in response to crossings of an amplitude threshold by the first cardiac electrical signal. The sensing circuit further includes a second sensing channel configured to receive a second cardiac electrical signal via a second extra-cardiovascular sensing electrode vector coupled to the extra-cardiovascular ICD and different than the first extra-cardiovascular sensing electrode vector. The control circuit is coupled to the sensing circuit and the memory and is configured to store a time segment of the second cardiac electrical signal in the memory in response an R-wave sensed by the first sensing channel, determine a morphology match score for stored time segments of the second cardiac electrical signal, and based on the morphology match scores, withhold detection of a tachyarrhythmia episode.

In another example, the disclosure provides a method performed by an extra-cardiovascular ICD including: sensing R-waves by a first sensing channel of a sensing circuit of the extra-cardiovascular ICD in response to crossings of an amplitude threshold by a first cardiac electrical signal, the first cardiac electrical signal received by the first sensing channel via a first extra-cardiovascular sensing electrode vector coupled to the extra-cardiovascular ICD; storing a time segment of a second cardiac electrical signal in response to an R-wave sensed by the first sensing channel, the second cardiac electrical signal received via a second extra-cardiovascular sensing electrode vector by a second sensing channel of the extra-cardiovascular ICD; determining by a control circuit of the ICD a morphology match score for stored time segments of the second cardiac electrical signal; and, based on the morphology match scores, withholding detection of a tachyarrhythmia episode.

In another example, the disclosure provides a non-transitory, computer-readable storage medium comprising a set of instructions which, when executed by a processor of an extra-cardiovascular ICD, causes the extra-cardiovascular ICD to sense R-waves by a first sensing channel of a sensing circuit of the extra-cardiovascular ICD in response to crossings of an amplitude threshold by a first cardiac electrical signal, the first cardiac electrical signal received by the first sensing channel via a first extra-cardiovascular sensing electrode vector coupled to the extra-cardiovascular ICD; store a time segment of a second cardiac electrical signal in response to an R-wave sensed by the first sensing channel, the second cardiac electrical signal received via a second extra-cardiovascular sensing electrode vector by a second sensing channel of the extra-cardiovascular ICD; determine by a control circuit of the ICD a morphology match score for stored time segments of the second cardiac electrical signal; and, based on the morphology match scores, withhold detection of a tachyarrhythmia episode.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting TWOS in a medical device system and withholding detection of a ventricular tachyarrhythmia in response to detecting TWOS. The medical device system may be any implantable or external medical device enabled for sensing cardiac electrical signals, including implantable pacemakers, implantable cardioverter-defibrillators (ICDs), cardiac resynchronization therapy (CRT) devices, or cardiac monitors coupled to extra-cardiovascular, transvenous, epicardial or intrapericardial leads carrying sensing electrodes; leadless pacemakers, ICDs or cardiac monitors having housing-based sensing electrodes; and external pacemakers, defibrillators, or cardiac monitors coupled to external, surface or skin electrodes.

However, the techniques are described in conjunction with an implantable medical lead carrying extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for detecting TWOS to promote reliable sensing of R-waves, attendant to ventricular depolarization, from a cardiac electrical signal acquired by the ICD via extra-cardiovascular electrodes to promote reliable detection of ventricular tachycardia (VT) and ventricular fibrillation (VF).

Figure 1A:
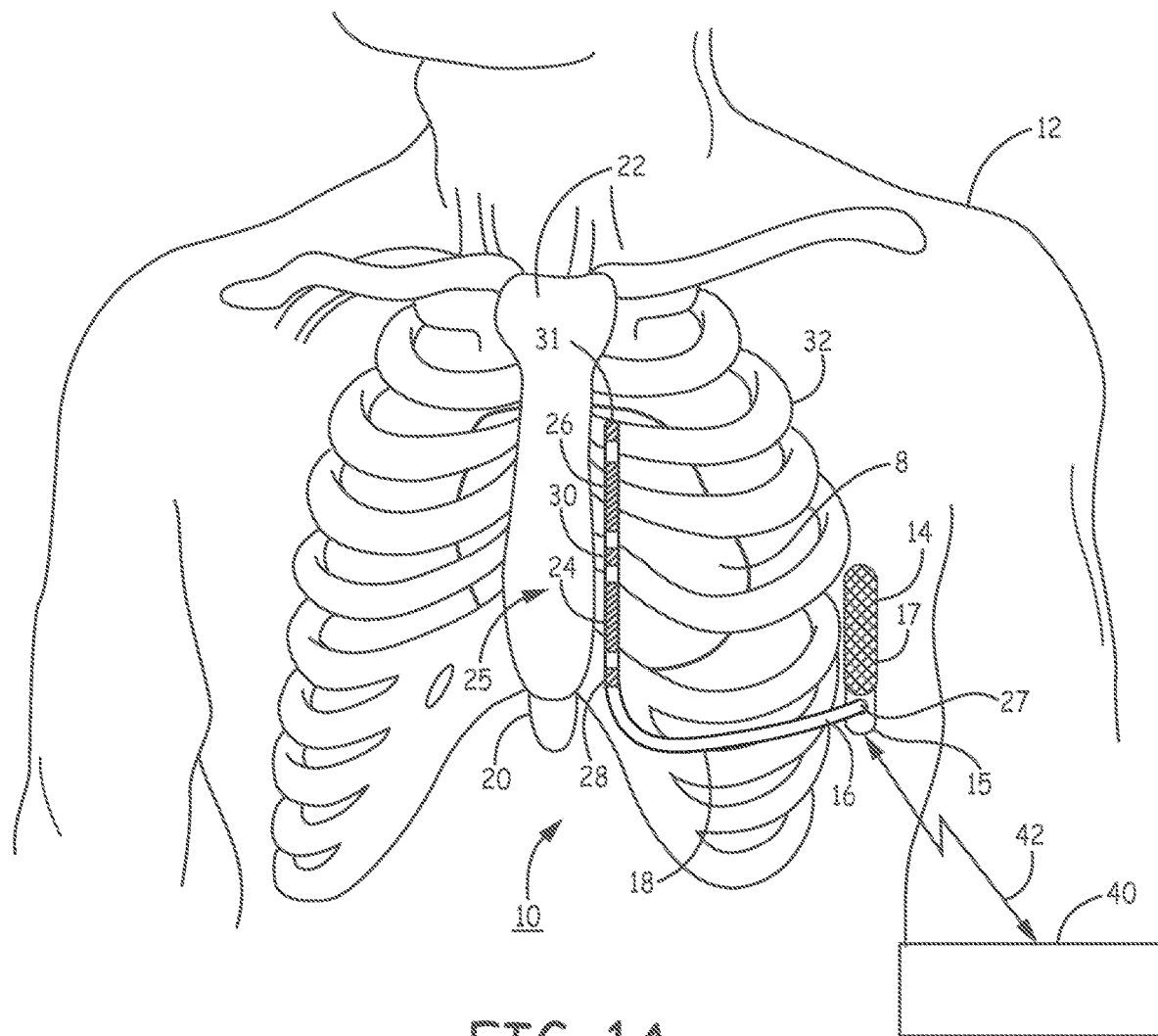
FIGS. 1A and 1B are conceptual diagrams of an extra-cardiovascular ICD system according to one example.
Figure 1B:
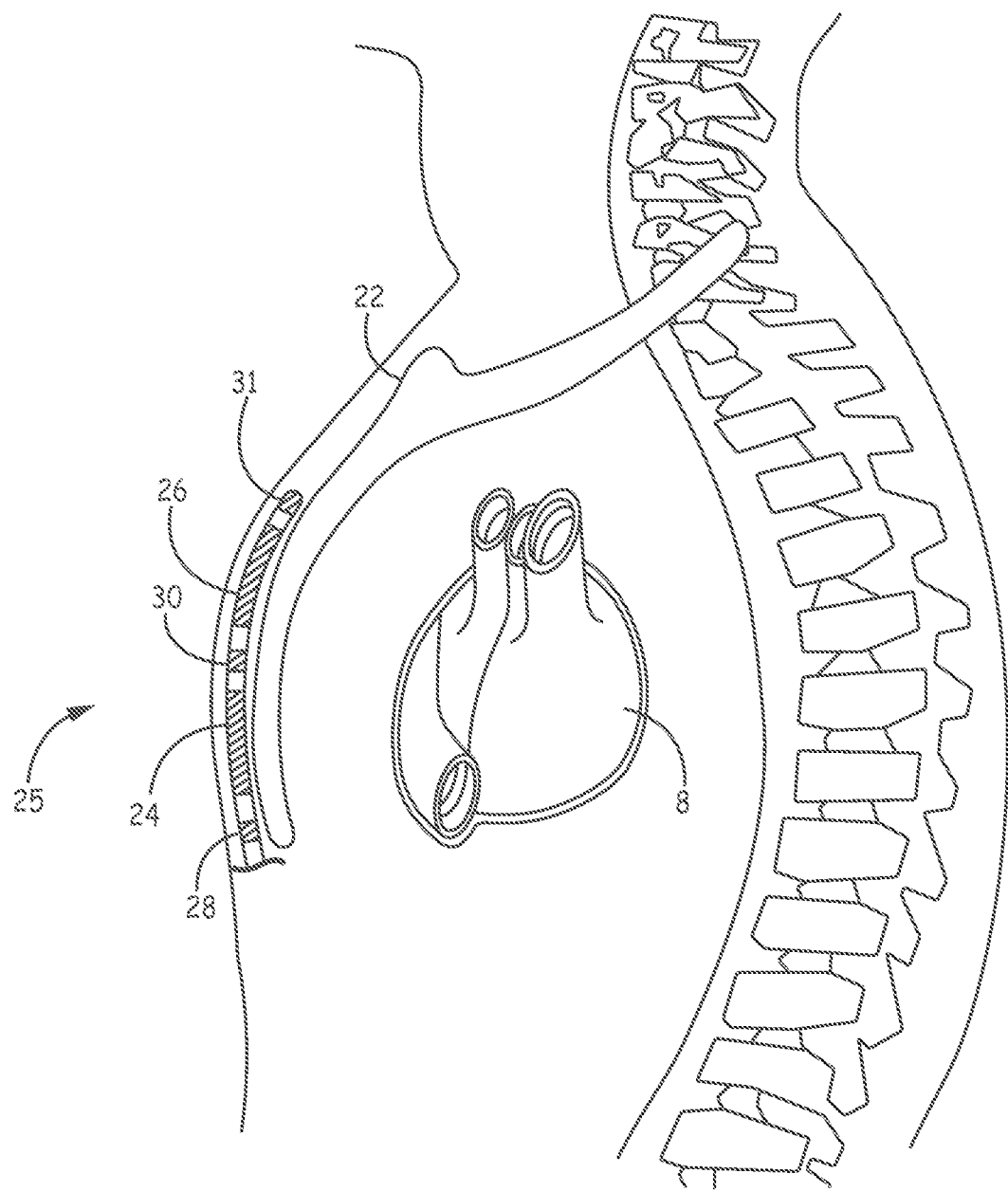

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a can electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals in conjunction with lead-based electrodes. In other instances, housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a pacing electrode vector for delivering extra-cardiovascular pacing pulses such as ATP pulses and/or in a sensing vector used to sense cardiac electrical signals and detect VT and VF.

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31, which may be separate respective insulated conductors within the lead body. The respective conductors electrically couple the electrodes 24, 26, 28, 30 and 31 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, VT or VF. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30 and between one of pace/sense electrodes 28 or 30 and housing 15, and ATP pulses are delivered between pace/sense electrode 30 used as a cathode electrode and defibrillation electrode 24 used as a return anode electrode. In other examples, pacing pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and pacing electrode vectors may be selected according to individual patient need.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program R-wave sensing parameters, cardiac rhythm detection parameters and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
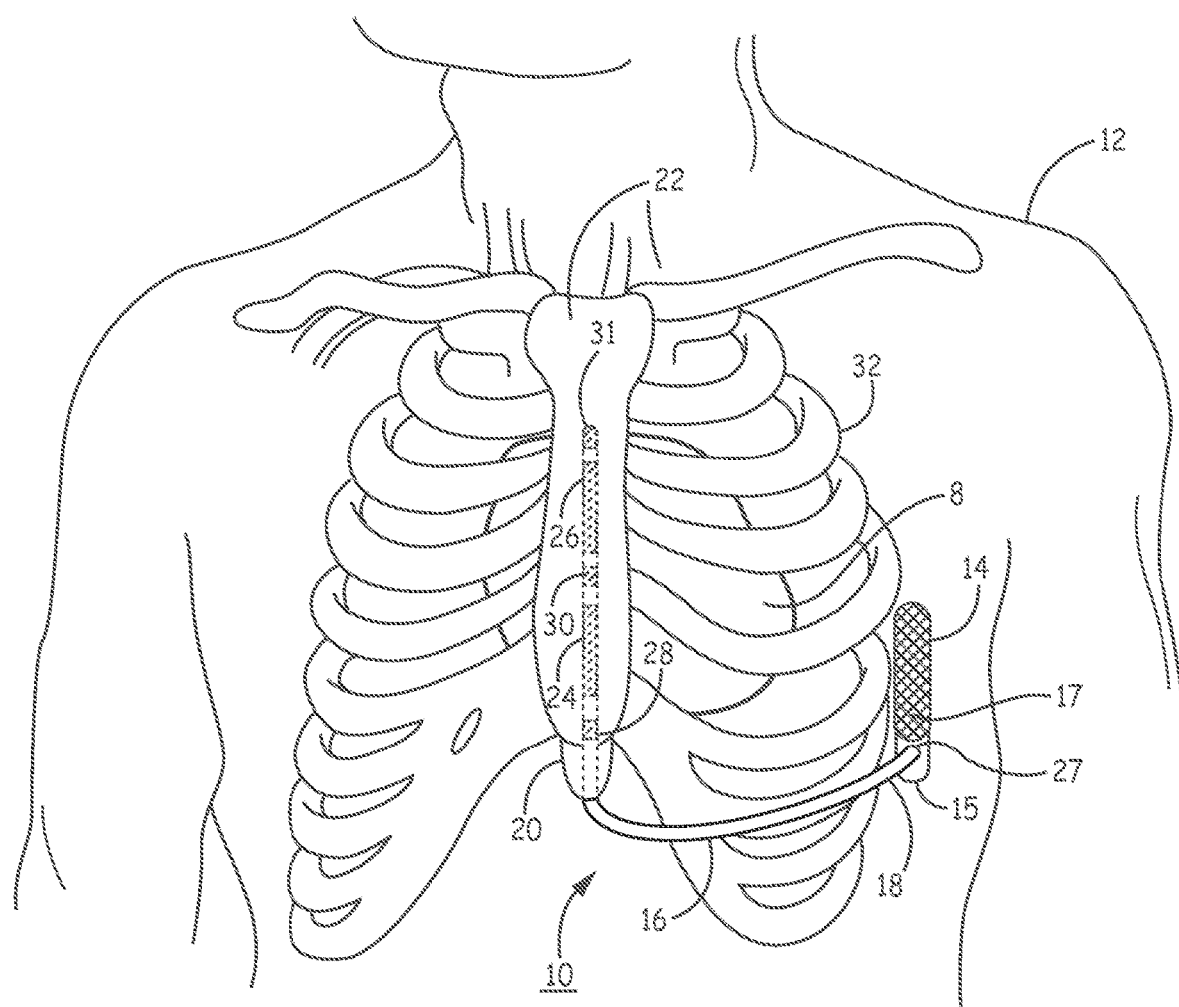
FIGS. 2A-2C are conceptual diagrams of a patient implanted with the extra-cardiovascular ICD system of FIG. 1A in a different implant configuration.
Figure 2B:
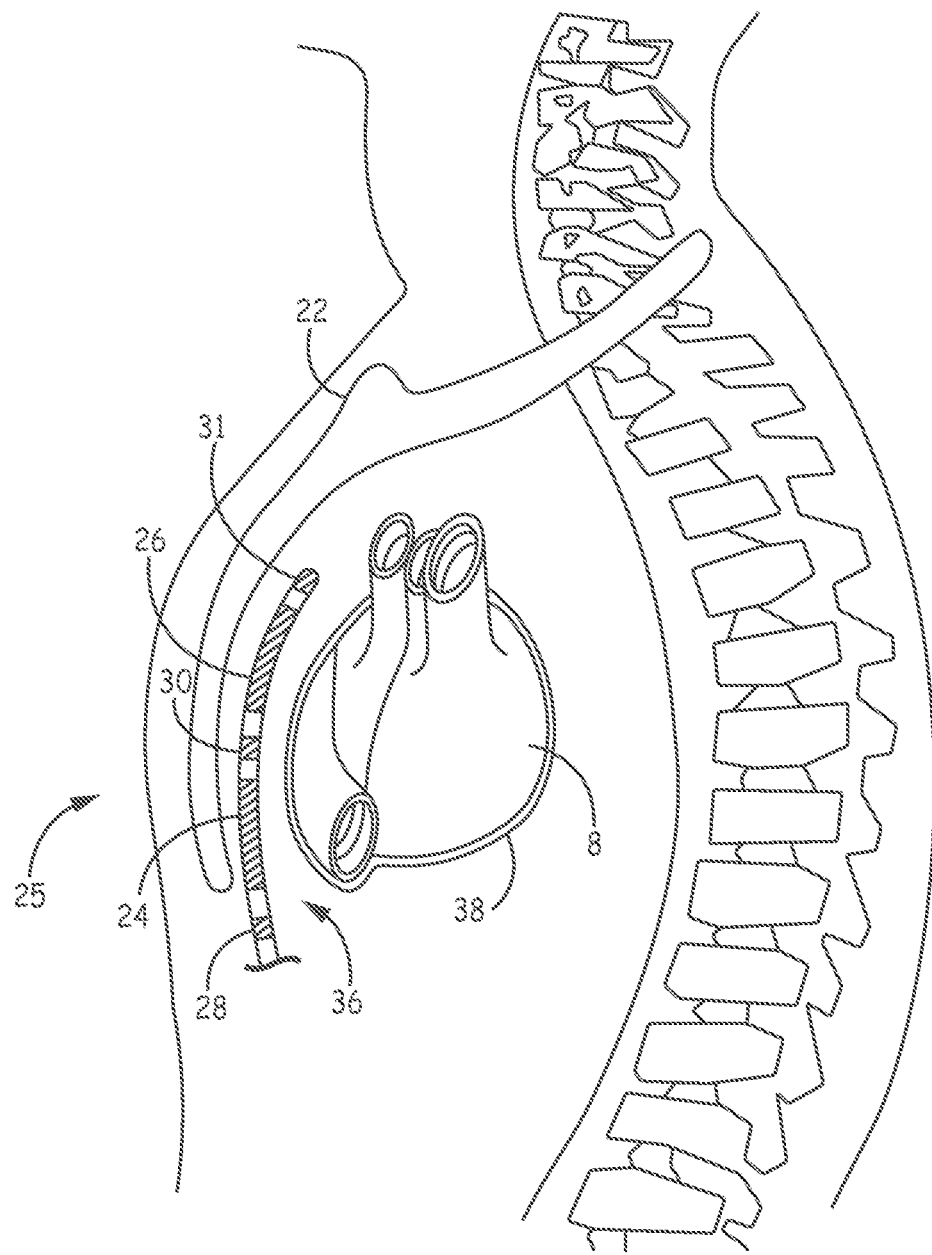
Figure 2C:
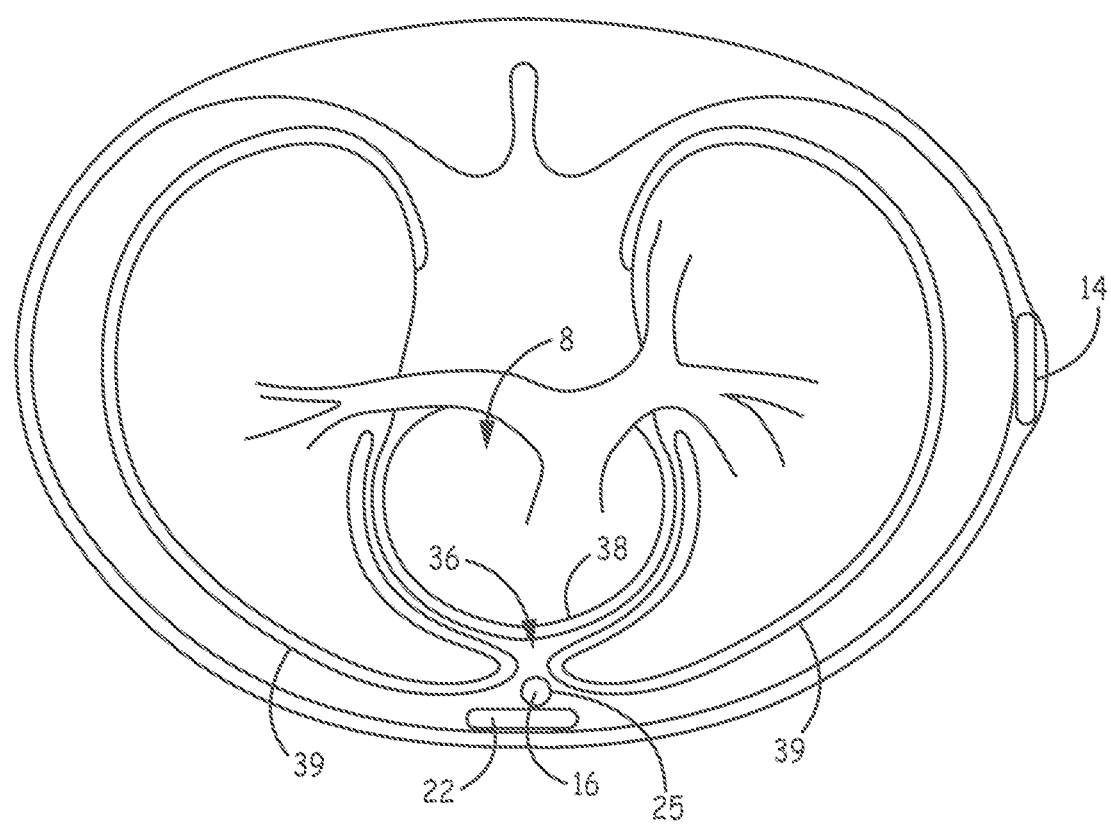

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the cardiac pacing techniques described herein are generally disclosed in the above-incorporated patent applications.

Figure 3:
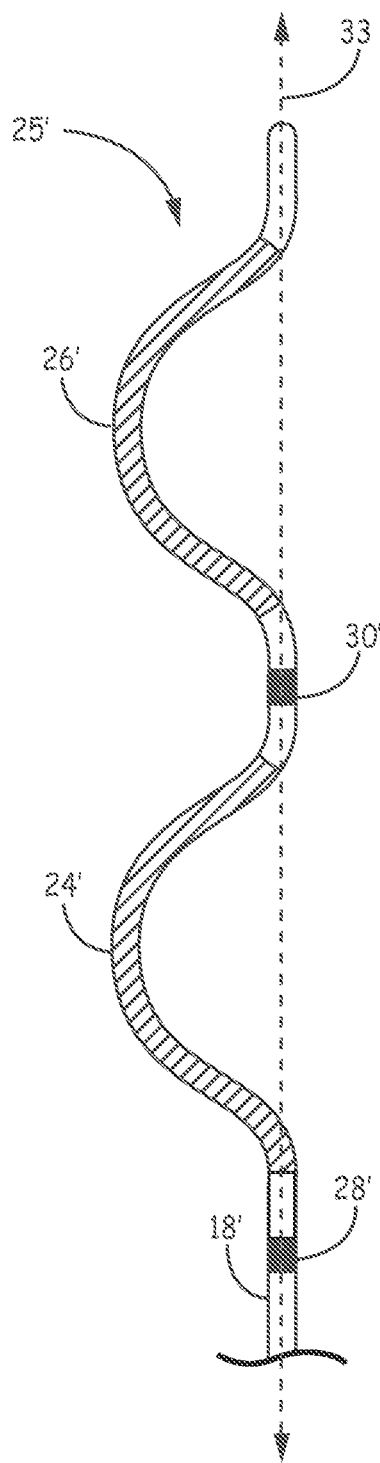
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in pre-grant U.S. Pat. Publication No. 2016/015856 (Marshall, et al.), incorporated herein by reference in its entirety.

Figure 4:
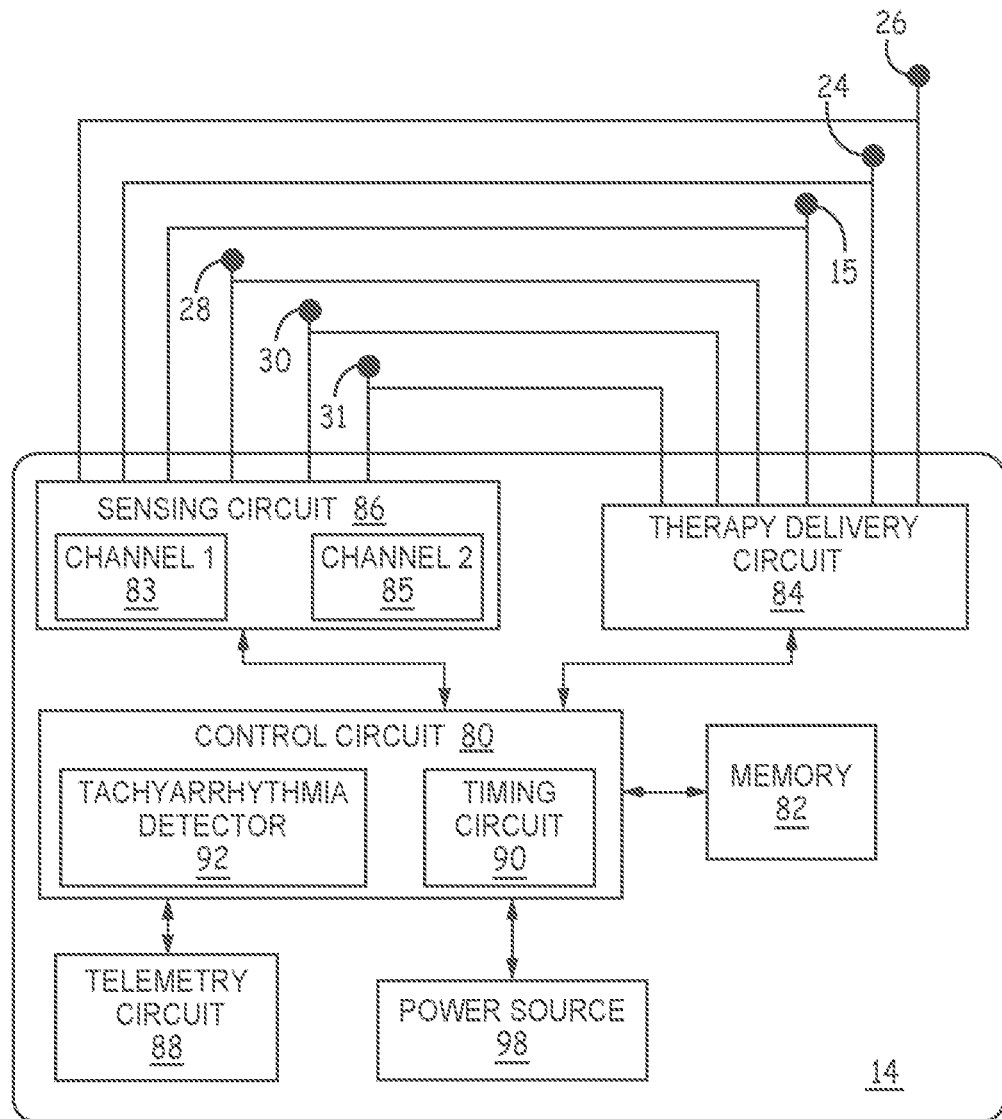
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT and VF for determining when ATP or CV/DF shocks are required. ICD 14 is coupled to an extra-cardiovascular lead, such as lead 16 carrying extra-cardiovascular electrodes 24, 26, 28, 30 and 31 (if present), for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering ATP, post-shock pacing or other pacing pulses instead of low voltage capacitors. Power source 98 is also coupled to components of sensing circuit 86, such as sense amplifiers, analog-to-digital converters, switching circuitry, etc. as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components. For example, cardiac event sensing and tachyarrhythmia detection operations may be performed by sensing circuit 86 under the control of control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 (if present as shown in FIGS. 1A and 2A) carried by lead 16 (e.g., as shown in FIGS. 1A-3) and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 is enabled to selectively receive cardiac electrical signals from at least two sensing electrode vectors from the available electrodes 24, 26, 28, 30, 31 and housing 15. At least two cardiac electrical signals from two different sensing electrode vectors may be received simultaneously by sensing circuit 86, and sensing circuit 86 may monitor one or both or the cardiac electrical signals at a time for sensing cardiac electrical signals. For example, sensing circuit 86 may include switching circuitry for selecting which of electrodes 24, 26, 28, 30, 31 and housing 15 are coupled to a sensing channel 83 or 85 including cardiac event detection circuitry, e.g., as described in conjunction with FIGS. 5 and 12. Switching circuitry may include a switch array, switch matrix, multiplexer, or any other type of switching device suitable to selectively couple components of sensing circuit 86 to selected electrodes. The cardiac event detection circuitry within sensing circuit 86 may include one or more sense amplifiers, filters, rectifiers, threshold detectors, comparators, analog-to-digital converters (ADCs), or other analog or digital components as described further in conjunction with FIGS. 5 and 12. A cardiac event sensing threshold may be automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86.

In some examples, sensing circuit 86 includes multiple sensing channels 83 and 85 for acquiring cardiac electrical signals from multiple sensing vectors selected from electrodes 24, 26, 28, 30, 31 and housing 15. Each sensing channel 83 and 85 may be configured to amplify, filter and digitize the cardiac electrical signal received from selected electrodes coupled to the respective sensing channel to improve the signal quality for detecting cardiac events, such as R-waves. For example, each sensing channel 83 and 85 may include a pre-filter and amplifier for filtering and amplifying a signal received from a selected pair of electrodes. The resulting raw cardiac electrical signal may be passed from the pre-filter and amplifier to cardiac event detection circuitry in at least one sensing channel 83 for sensing cardiac events from the received cardiac electrical signal in real time. As disclosed herein, sensing channel 83 may be configured to sense cardiac events such as R-waves based on a cardiac event sensing threshold, and second sensing channel 85 may be configured to pass a digitized cardiac electrical signal obtained from a different sensing electrode vector to control circuit 80 for use in confirming a cardiac event sensed by first sensing channel 83.

Upon detecting a cardiac event based on a sensing threshold crossing, first sensing channel 83 may produce a sensed event signal, such as an R-wave sensed event signal, that is passed to control circuit 80. The sensed event signal is used by control circuit 80 to trigger storage of a time segment of the second cardiac electrical signal for post-processing and analysis for confirming the R-wave sensed event signal as described below, e.g., in conjunction with FIGS. 7 through 9. Memory 82 may be configured to store a predetermined number of cardiac electrical signal segments in circulating buffers under the control of control circuit 80, e.g., at least one, two or other number of cardiac electrical signal segments. Each segment may be written to memory 82 over a time interval extending before and after the R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection.

The R-wave sensed event signals are also used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia episodes. Tachyarrhythmia detector 92 may be implemented in control circuit 80 as hardware and/or firmware that processes and analyzes signals received from sensing circuit 86 for detecting VT and/or VF. In some examples, the timing of R-wave sense event signals received from sensing circuit 86 is used by timing circuit 90 to determine RRIs between sensed event signals. Tachyarrhythmia detector 92 may include comparators and counters for counting RRIs determined by timing circuit 92 that fall into various rate detection zones for determining a ventricular rate or performing other rate- or interval-based assessment for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. When an interval counter reaches a detection threshold, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria. Examples of other parameters that may be determined from cardiac electrical signals received by sensing circuit 86 for determining the status of tachyarrhythmia detection rejection rules that may cause withholding to a VT or VF detection are described in conjunction with FIGS. 10, 11 and 13.

To support these additional analyses, sensing circuit 86 may pass a digitized electrocardiogram (ECG) signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82. Memory 82 may include one or more circulating buffers to temporarily store digital cardiac electrical signal segments for analysis performed by control circuit 80 to confirm R-waves sensed by sensing channel 83, determine morphology matching scores, detect T-wave oversensing, detect noise contamination, and more as further described below.

Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. Examples of devices and algorithms that may be adapted to utilize techniques for R-wave sensing and confirmation and tachyarrhythmia detection described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry; one or more charge storage devices, such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within timing circuit 90 are reset upon sensing of R-waves as indicated by signals from sensing circuit 86. In accordance with the selected mode of pacing, pacing pulses are generated by a pulse output circuit of therapy delivery circuit 84 when an escape interval counter expires. The pace output circuit is coupled to the desired pacing electrodes via a switch matrix for discharging one or more capacitors across the pacing load. The escape interval counters are reset upon generation of pacing pulses, and thereby control the basic timing of cardiac pacing functions, including ATP. The durations of the escape intervals are determined by control circuit 80 via a data/address bus. The value of the count present in the escape interval counters when reset by sensed R-waves can be used to measure RRIs by timing circuit 90 as described above for detecting the occurrence of a variety of arrhythmias by tachyarrhythmia detector 92.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92 for predicting or diagnosing an arrhythmia.

In response to the detection of ventricular tachycardia, ATP therapy can be delivered by loading a regimen from the microprocessor included in control circuit 80 into timing circuit 90 according to the type and rate of tachycardia detected. In the event that higher voltage cardioversion or defibrillation pulses are required, e.g., the tachyarrhythmia is VF or the VT is not terminated via the ATP therapy, the control circuit 80 activates cardioversion and defibrillation control circuitry included in control circuit 80 to initiate charging of the high voltage capacitors via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by control circuit 80, a logic signal is generated on a capacitor full line passed to therapy delivery circuit 84, terminating charging. The defibrillation or cardioversion pulse is delivered to the heart under the control of the timing circuit 90 by an output circuit of therapy delivery circuit 84 via a control bus. The output circuit determines the electrodes used for delivering the cardioversion or defibrillation pulse and the pulse wave shape. Therapy delivery and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
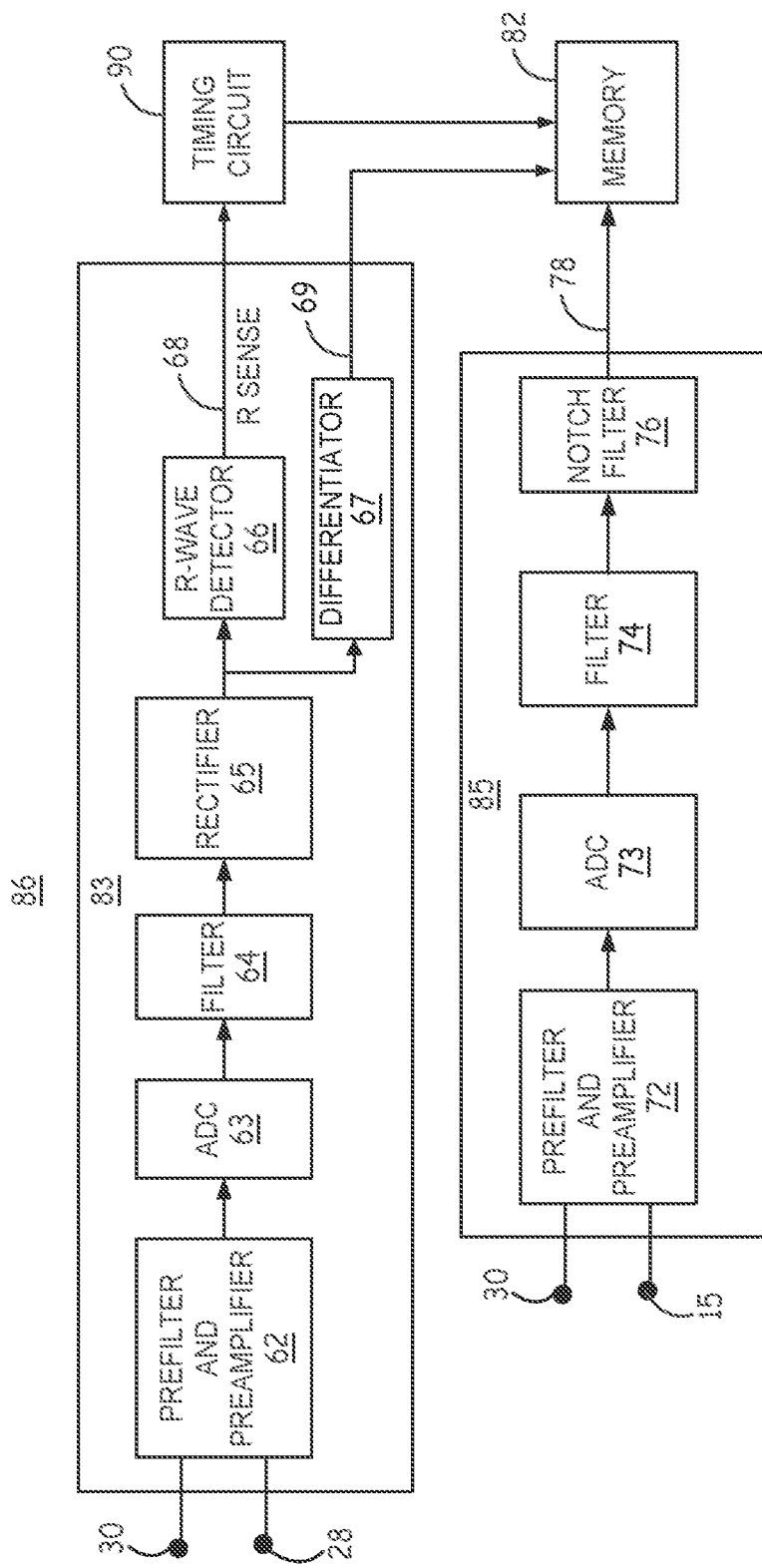
FIG. 5 is diagram of circuitry included in the sensing circuit of FIG. 4 according to one example.

FIG. 5 is diagram of circuitry included in first sensing channel 83 and second sensing channel 85 of sensing circuit 86 according to one example. First sensing channel 83 may be selectively coupled via switching circuitry (not shown) to a first sensing electrode vector including electrodes carried by extra-cardiovascular lead 16 as shown in FIGS. 1A-2C for receiving a first cardiac electrical signal. First sensing channel 83 may be coupled to a sensing electrode vector that is a short bipole, having a relatively shorter inter-electrode distance or spacing than the second electrode vector coupled to second sensing channel 85. In the example shown, the first sensing electrode vector may include pace/sense electrodes 28 and 30. In other examples, the first sensing electrode vector coupled to sensing channel 83 may include pace/sense electrodes 30 and 31 and in some cases pace/sense electrodes 28 and 31 depending on the inter-electrode spacing and position of the distal portion 25 of lead 16. In other examples, the first sensing channel 83 may be selectively coupled to a sensing electrode vector including a defibrillation electrode 24 and/or 26, e.g., a sensing electrode vector between pace/sense electrode 28 and defibrillation electrode 24, between pace/sense electrode 30 and either of defibrillation electrodes 24 or 26, or between pace/sense electrode 26 and 31, for example. In some examples, the first sensing electrode vector may be between defibrillation electrodes 24 and 26.

Sensing circuit 86 includes a second sensing channel 85 that receives a second cardiac electrical signal from a second sensing vector, for example from a vector that includes electrode 30 and housing 15, as shown, or a vector that includes electrode 28 and housing 15. Second sensing channel 85 may be selectively coupled to other sensing electrode vectors, which may form a long bipole having an inter-electrode distance or spacing that is greater than the sensing electrode vector coupled to first sensing channel 83. As described below, the second cardiac electrical signal received by second sensing channel 85 via a long bipole may be used by control circuit 80 for morphology analysis (including beat morphology analysis, noise rejection and other analysis, for example as described in conjunction with FIG. 10). In other examples, any vector selected from the available electrodes, e.g., electrodes 24, 26, 28, 30 and/or 31 and/or housing 15 may be included in a sensing electrode vector coupled to second sensing channel 85.

The electrical signals developed across input electrodes 28 and 30 of sensing channel 83 and across input electrodes 30 and 15 of sensing channel 85 are provided as differential input signals to the pre-filter and pre-amplifiers 62 and 72, respectively. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In sensing channel 83, the digital output of ADC 63 is passed to filter 64 which may be a digital bandpass filter have a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold.

The R-wave sensing threshold may be controlled by sensing circuit 86 and/or control circuit 80 to be a multi-level sensing threshold as disclosed in U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval equal to a tachycardia detection interval, then drops to a second sensing threshold value held until a drop time interval expires, which may be 1 to 2 seconds long. The sensing threshold drops to a minimum sensing threshold after the drop time interval. The starting sensing threshold value may be the lower of a predetermined percentage of the most recent, preceding sensed R-wave peak amplitude and a maximum sensing threshold limit determined using a sensitivity-dependent gain and the programmed sensitivity setting. In other examples, the R-wave sensing threshold used by R-wave detector 66 may be set to a starting value based on a preceding R-wave peak amplitude and decay linearly or exponentially over time until reaching a minimum sensing threshold. However, the techniques of this application are not limited to a specific behavior of the sensing threshold. Instead, other automatically adjusted sensing thresholds may be utilized.

In some examples, the filtered, digitized cardiac electrical signal from sensing channel 83 (output of filter 64) may be stored in memory 82 for signal processing by control circuit 80 for use in detecting tachyarrhythmia episodes. In one example, the output of rectifier 64 is passed to differentiator 67 which determines an Nth order differential signal 69 that is passed to memory 82. Control circuit 80 may retrieve the stored signal from memory 82 for performing signal analysis by tachyarrhythmia detector 92 according to implemented tachyarrhythmia detection algorithms. For example, a T-wave oversensing algorithm implemented in tachyarrhythmia detector 92 may detect evidence of T-wave oversensing from a first order differential signal 69 produced by differentiator 67 as described below in conjunction with FIGS. 14 and 15. Examples of methods for detecting T-wave oversensing using a differential signal may be performed by tachyarrhythmia detector 92 as generally disclosed in U.S. Pat. No. 7,831,304 (Cao, et al.), incorporated herein by reference in its entirety.

The second cardiac electrical signal, digitized by ADC 73, may be passed to filter 74 for bandpass filtering, e.g., from 10 Hz to 30 Hz. In some examples, sensing channel 85 includes notch filter 76. Notch filter 76 may be implemented in firmware or hardware and is provided to attenuate 50-60 Hz electrical noise, muscle noise and other electromagnetic interference (EMI) or electrical noise/artifacts in the second cardiac electrical signal. Cardiac electrical signals acquired using extra-cardiovascular electrodes as shown, for example in FIGS. 1A-3, may be more likely to be contaminated by 50-60 Hz electrical noise, muscle noise and other EMI, electrical noise/artifacts than intra-cardiac electrodes. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies. One example of a notch filter, designed with minimal computational requirements, and its filtering characteristics are described in conjunction with FIG. 6.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment is analyzed by control circuit 80 on a triggered, as needed basis, as described in conjunction with FIGS. 7-13 to confirm R-waves sensed by the first sensing channel 83.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sense event signal 68 prior to filtering by notch filter 76. When control circuit 80 is triggered to analyze the stored, second cardiac electrical signal for confirming an R-wave sensed event signal, for example as described in conjunction with FIGS. 7, 10, 11 and 13, the notch filter 76 may be applied to the stored segment of the second cardiac electrical signal before further processing and analysis of the stored segment. In this way, if analysis of the stored signal segment is not required for confirming an R-wave sensed by first sensing channel 83, firmware implemented to perform the operation of notch filter 76 need not be executed.

The configuration of sensing channels 83 and 85 is illustrative in nature and should not be considered limiting of the techniques described herein. The sensing channels 83 and 85 of sensing circuit 86 may include more or fewer components than illustrated and described in FIG. 5. First sensing channel 83, however, is configured to detect R-waves in real time, e.g., in hardware implemented components, from a first cardiac electrical signal based on crossings of an R-wave sensing threshold by the first cardiac electrical signal, and second sensing channel 85 is configured to provide a second cardiac electrical signal for storage in memory 82 for post-processing and analysis by control circuit 80 for confirming R-wave sensed event signals produced by the first sensing channel 83.

Figure 6:
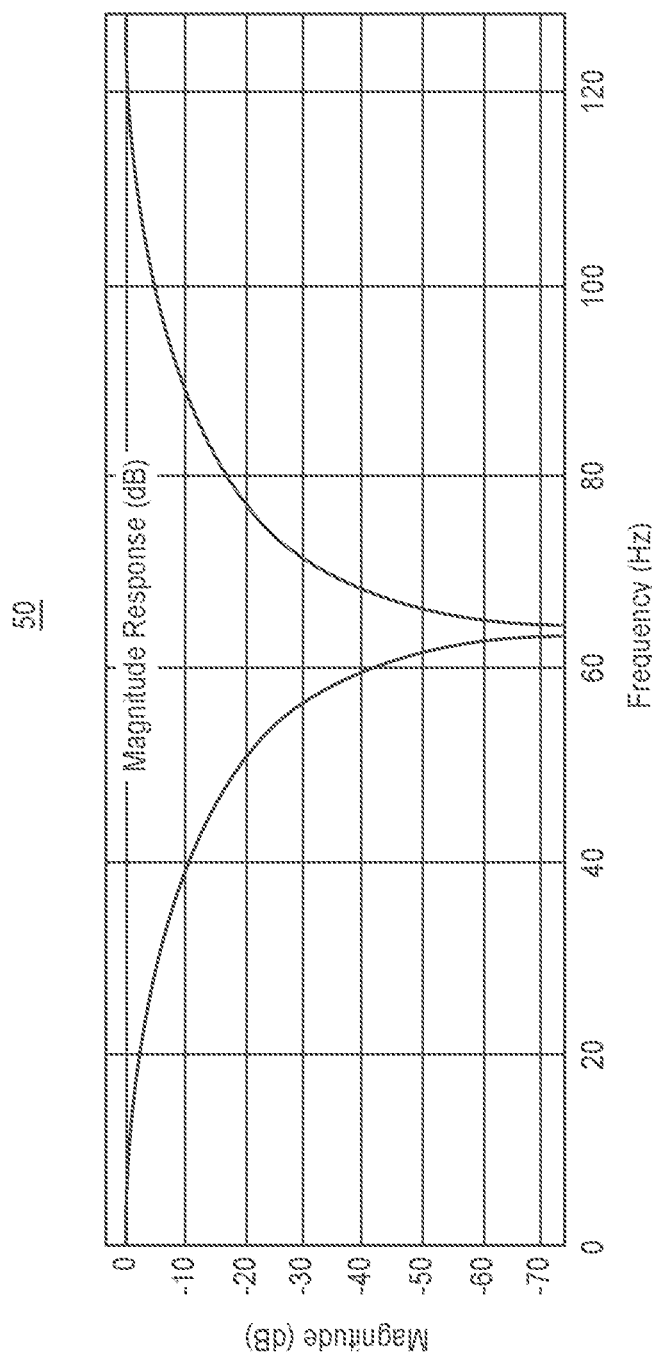
FIG. 6 is a plot of the attenuation characteristics of a notch filter that may be included in the sensing circuit of FIG. 5.

FIG. 6 is a plot 50 of the attenuation characteristics of notch filter 76 of the second sensing channel 85. In one example, notch filter 76 is implemented in firmware as a digital filter. The output of the digital notch filter may be determined by firmware implemented in the second sensing channel 85 according to the equation:

$$Y(n) = (x(n) + 2x(n-2) + x(n-4))/4 \qquad \text{a.}$$

where $x(n)$ is the amplitude of the nth sample point of the digital signal received by the notch filter 76, $x(n-2)$ is the amplitude of the n−2 sample point, and $x(n-4)$ is the amplitude of the n−4 sample point for a sampling rate of 256 Hz. $Y(n)$ is the amplitude of the nth sample point of the notch-filtered, digital second cardiac electrical signal. The plot 50 of FIG. 6 represents the resulting attenuation of the amplitude $Y(n)$ as a function of frequency. At a frequency of 60 Hz, the attenuation of the magnitude of $Y(n)$ is −40 decibels (dB). At a frequency of 50 Hz, the attenuation is −20 dB, and at 23 Hz, which may be typical of an R-wave of the cardiac electrical signal, the attenuation is limited to −3 dB. Notch filter 76 may therefore provide highly attenuated 50 and 60 Hz noise, muscle noise, other EMI, and other electrical noise/artifacts while passing lower frequency cardiac signals in the second cardiac electrical signal output of sensing channel 85. Although the notch filter 76 may not attenuate frequencies approaching the maximum frequency of 128 Hz, filter 74 of second sensing channel 85, which may be a bandpass filter, may adequately reduce the higher frequency range signal content above 60 Hz.

The sample point numbers indicated in the equation above for determining a notch-filtered signal may be modified as needed when a different sampling rate other than 256 Hz is used, however, the resulting frequency response may or may not be the same as that shown in FIG. 6. The notch filter 76 uses minimal computations with only two adds and three shifts required. In other examples, other digital filters may be used for attenuation of 50 and 60 Hz. For example, for a sampling rate of 256 Hz, a filtered signal $Y(n)$ may be determined as $Y(n) = (x(n) + x(n-1) + x(n-2) + x(n-3))/4$ which has less attenuation at 50 and 60 Hz than the frequency response shown in FIG. 6 but acts as a low-pass, notch filter with greater attenuation at higher frequencies (greater than 60 Hz) than the frequency response shown FIG. 6.

Figure 7:
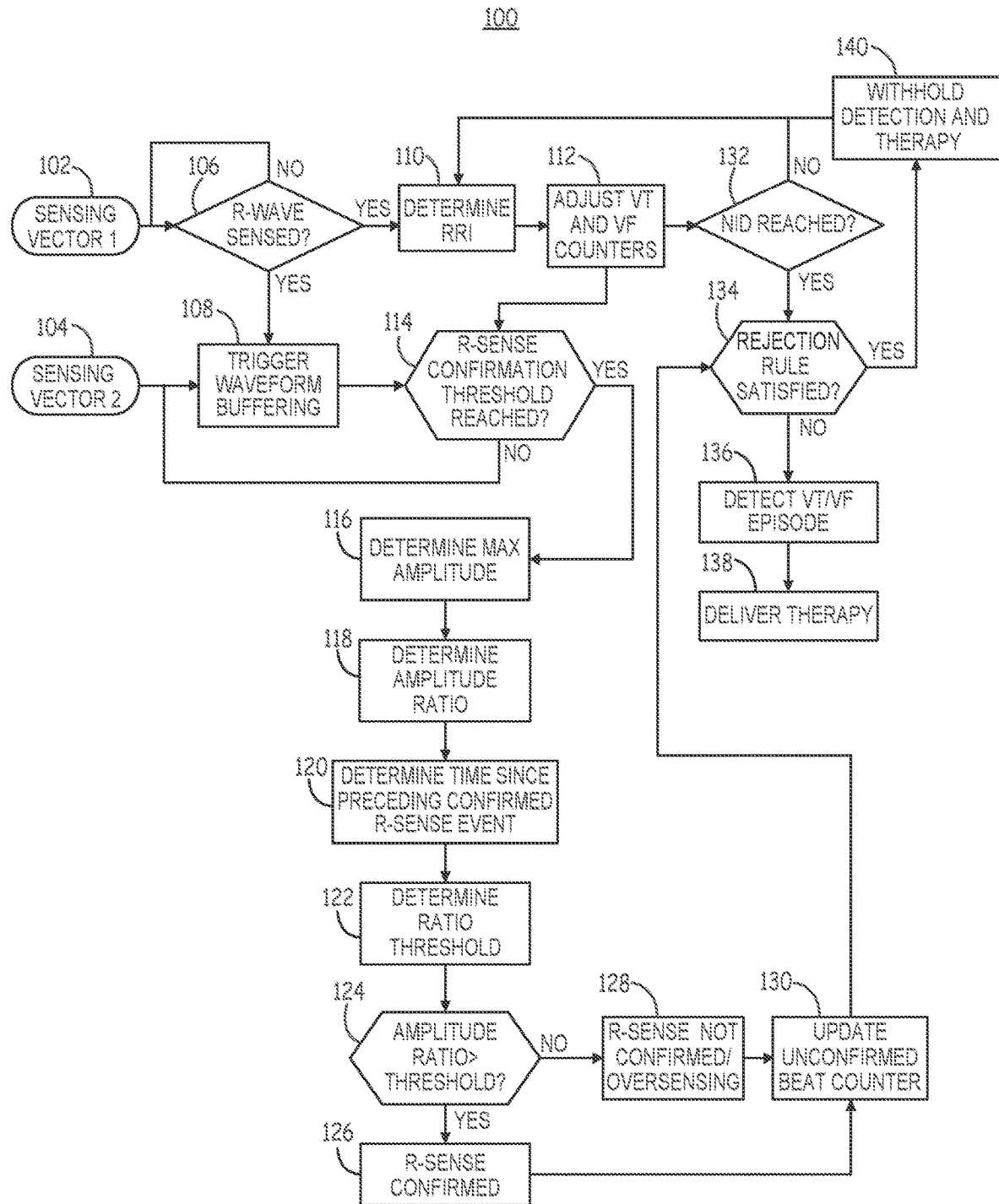
FIG. 7 is a flow chart of a method performed by the ICD of FIGS. 1A-2C for sensing and confirming R-waves for use in tachyarrhythmia detection according to one example.

FIG. 7 is a flow chart 100 of a method performed by ICD 14 for sensing and confirming R-waves for use in tachyarrhythmia detection according to one example. At blocks 102 and 104, two different sensing electrode vectors are selected by sensing circuit 86 for receiving a first cardiac electrical signal by a first sensing channel 83 and a second cardiac electrical signal by a second sensing channel 85. The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

The first sensing vector selected at block 102 for obtaining a first cardiac electrical signal may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers compared to other available sensing electrode pairs. The first sensing vector may be a vertical sensing vector (with respect to an upright or standing position of the patient) or approximately aligned with the cardiac axis for maximizing the amplitude of R-waves in the first cardiac electrical signal for reliable R-wave sensing.

The second sensing electrode vector used to obtain a second cardiac electrical signal at block 104 may be a relatively long bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This sensing vector may be orthogonal or almost orthogonal to the first sensing vector in some examples, but the first and second sensing vectors are not required to be orthogonal vectors. The second sensing electrode vector may provide a relatively more global or far-field cardiac electrical signal compared to the first sensing electrode vector. The second cardiac electrical signal obtained at block 104 may be used for waveform morphology analysis by the tachyarrhythmia detector 92 of control circuit 80 and is used for cardiac signal analysis for confirming an R-wave sensed event signal produced by first sensing channel 83 of sensing circuit 86.

Sensing circuit 86 may produce an R-wave sensed event signal at block 106 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 106, control circuit 80 is triggered at block 108 to store a segment of the second cardiac electrical signal received from the second sensing channel 85 (sensing vector 2, block 104) in a circulating buffer of memory 82. A digitized segment of the second cardiac electrical signal may be 100 to 500 ms long, for example, including sample points before and after the time of the R-wave sensed event signal, which may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the cardiac electrical signal is at least 50 sample points obtained at a sampling rate of 256 Hz, or about 200 ms. In another example, the buffered segment is at least 92 sample points, or approximately 360 ms, sampled at 256 Hz and is available for morphology analysis, noise analysis, T-wave oversensing, and/or other analysis performed by tachyarrhythmia detector 92 for detecting VT or VF. Other analyses of the buffered second cardiac electrical signal that may be performed by tachyarrhythmia detector 92 for detecting VT or VF, or withholding detection of VT or VF, are described in conjunction with FIG. 10. Memory 82 may be configured to store a predetermined number of second cardiac electrical segments, e.g., at least 1 and in some cases two or more cardiac electrical signal segments, in circulating buffers such that the oldest segment is overwritten by the newest segment. However, previously stored segments may never be analyzed for R-wave confirmation before being overwritten if an R-wave confirmation threshold is not reached as described below. In some examples, a single segment of the second cardiac electrical signal may be stored and if not needed for confirming an R-wave sensed by the first channel, the segment is overwritten by the next segment corresponding to the next R-wave sensed event signal.

In addition to buffering a segment of the second cardiac electrical signal, control circuit 80 responds to the R-wave sensed event signal produced at block 106 by determining an RRI at block 110 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 112. If the RRI is longer than a tachycardia detection interval (TDI), the tachyarrhythmia interval counters remain unchanged. If the RRI is shorter than the TDI but longer than a fibrillation detection interval (FDI), i.e., if the RRI is in a tachycardia detection interval zone, a VT interval counter is increased at block 112. If the RRI is shorter than or equal to the FDI, a VF interval counter is increased at block 112. In some examples, a combined VT/VF interval counter is increased if the RRI is less than the TDI.

After updating the tachyarrhythmia interval counters at block 112, tachyarrhythmia detector 92 compares the counter values to an R-sense confirmation threshold at block 114 and to VT and VF detection thresholds at block 132. If a VT or VF detection interval counter has reached an R-sense confirmation threshold, "yes" branch of block 114, the second cardiac electrical signal from sensing channel 85 is analyzed to confirm the R-wave sensed at block 106 by the first sensing channel 83. The R-sense confirmation threshold may be a VT or VF interval count that is greater than or equal to a count of one or another higher count value. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of intervals required to detect VT or VF. In addition or alternatively to applying an R-sense confirmation threshold to the individual VT and VF counters, an R-sense confirmation threshold may be applied to a combined VT/VF interval counter.

If the R-sense confirmation threshold is not reached by any of the tachyarrhythmia interval counters at block 114, the control circuit 80 waits for the next R-wave sensed event signal at block 108 to buffer the next segment of the second cardiac electrical signal. If the R-sense confirmation threshold is reached at block 114, the control circuit 80 determines a maximum amplitude at block 116 of the buffered signal segment stored for the most recent R-wave sensed event signal. The maximum amplitude may be determined from a differential signal determined from the buffered signal segment. For example, an nth-order differential signal may be determined from the buffered signal segment by determining a difference between the ith and the ith-n signal sample points of the buffered signal segment. In one example a 4th order differential signal is determined.

The maximum absolute value of the differential signal is estimated as the amplitude of the event in the second cardiac electrical signal that was sensed as an R-wave from the first cardiac electrical signal. The time of the maximum absolute value of the signal is identified as the time of the event in the second cardiac electrical signal. When the R-wave is not the first R-wave to be confirmed since the R-sense confirmation threshold was reached, the control circuit 80 determines an amplitude ratio at block 118 as the ratio of the maximum absolute value determined at block 116 to the event amplitude determined from the second cardiac electrical signal for the most recently confirmed R-wave sensed event. At block 120, the control circuit 80 determines a time interval from the most recent event of the second cardiac electrical signal confirmed as an R-wave sensed event to the time of the event determined at block 116.

When the R-wave is the first R-wave to be confirmed after the R-sense confirmation threshold is reached, the first confirmed event on the second cardiac electrical signal may be assumed to occur at the same time as the R-wave sensed event signal with a default maximum amplitude. The default maximum amplitude may be set equal to the amplitude of the R-wave sensed by the first sensing channel 83, a nominal value, e.g., 1 millivolt, or a previously determined R-wave amplitude or average R-wave amplitude determined from the second cardiac electrical signal. Alternatively, the maximum absolute amplitude of the differential signal and its time may be identified and stored as initial values used for determining an amplitude ratio and time at blocks 118 and 120 for the next R-wave to be confirmed. In other examples, an amplitude ratio may be determined for the first R-wave to be confirmed after the R-sense confirmation threshold is reached using a previously determined R-wave amplitude, e.g., from a prior time that the R-sense confirmation threshold was reached or a default R-wave amplitude. The first R-wave may be confirmed based on this amplitude ratio and/or time since the preceding R-wave sensed event signal.

At block 122, the control circuit 80 determines a ratio threshold to be applied to the amplitude ratio based on the time interval determined at block 120. In one example, the ratio threshold is retrieved from a look-up table stored in memory. In other examples, the ratio threshold may be computed as a function of the time interval determined at block 120. The ratio threshold may be a variable threshold that decreases as the time interval since the most recent confirmed R-wave increases. As such, the time interval determined at block 120 is used to determine what ratio threshold should be applied to the amplitude ratio determined at block 118 for confirming the R-wave sensed by first sensing channel 83. The ratio threshold may decrease in a linear, exponential or stepwise manner, or a combination thereof. For instance, the ratio threshold may decrease with a continuous slope or decay rate over some portions of time since the most recent confirmed R-wave and may be held constant over other portions of time since the most recent confirmed R-wave. An example of a time-varying ratio threshold and method for determining the ratio threshold at block 122 is described in conjunction with FIGS. 8 and 9.

At block 124, control circuit 80 compares the ratio threshold determined at block 122 to the amplitude ratio determined at block 118. If the amplitude ratio is equal to or greater than the ratio threshold, the R-wave sensed event is confirmed at block 126. If the amplitude ratio is less than the ratio threshold, the R-wave sensed event is not confirmed at block 128. The event may be an oversensed T-wave, P-wave, muscle noise, electromagnetic interference or other or non-cardiac electrical noise that has been oversensed by the first sensing channel 83.

At block 130 the control circuit 80 adjusts an unconfirmed beat counter. If the R-wave sensed event is not confirmed, the unconfirmed beat counter is increased by one count. If the R-wave sensed event is confirmed at block 126, the unconfirmed beat counter may kept at its current value or decreased. In some examples, the unconfirmed beat counter tracks how many out of the most recent predetermined number of consecutive R-wave sensed event signals produced by first sensing channel 83 are not confirmed in an x out of y manner. For example, the unconfirmed beat counter may track how many out of the most recent 12 R-wave sensed event signals are not confirmed to be R-waves based on the amplitude ratio comparison made at block 124.

In addition to counting how many beats are unconfirmed at block 130, data relating to the most recent n events analyzed by control circuit 80 may be stored in a rolling buffer. For example, data may be stored for the most recent twelve events analyzed for confirming an R-wave sensed event signal. The stored data may include the event amplitude, the amplitude ratio, the event timing, the time interval since the most recent confirmed event, and whether the event was confirmed or not confirmed.

While the R-wave sensed event signal is either confirmed or not confirmed based on an amplitude ratio determined from the second cardiac electrical signal according to the example of FIG. 7, it is recognized that other features of the second cardiac signal may be compared to R-wave confirmation criteria in addition to or instead of the event amplitude as described above. For example, a peak slew rate, an event area, an event signal width, or other features of the buffered cardiac electrical signal segment may be compared to respective thresholds for confirming the event as being an R-wave. The thresholds may be defined as a minimum ratio of the feature relative to an analogous feature of the most recent preceding event confirmed to be an R-wave or may be thresholds compared directly to features determined from the buffered cardiac electrical signal segment independent of preceding events.

If any of the tachyarrhythmia interval counters adjusted at block 112 reach a number of intervals to detect (NID) tachyarrhythmia, as determined at block 132, tachyarrhythmia detector 92 of control circuit 80 determines whether a rejection rule is satisfied at block 134 before detecting the tachyarrhythmia. In one example, the NID required to detect VT may be a count of 16 VT intervals, which are RRIs that fall into a predetermined VT interval range or zone. The NID to detect VF may be a count of 30 VF intervals out of the last 40 RRIs where the VF intervals are RRIs that fall into a predetermined VF interval range or zone. If an NID is reached, one or more rejection rules may be applied for rejecting a VT or VF detection based on RRI counts satisfying the NID. Various rejection rules are described below, e.g., in conjunction with FIGS. 10, 11 and 13. At least one rejection rule may relate to the number of R-waves sensed by the first sensing channel 83 that were not confirmed by the analysis of the second cardiac electrical signal. Another rejection rule may relate to the detection of TWOS as described in conjunction with FIGS. 14 through 16.

For instance, the unconfirmed beat counter updated at block 130 may be compared to a rejection rule criterion at block 134. The rejection rule criterion may be a rejection threshold requiring that at least x of y events are not confirmed R-waves. For example, if at least 3, at least 4, at least 6 or other predetermined number of the most recent 12 events (or other predetermined number of events) analyzed for confirming an R-wave sensed event signal are not confirmed R-waves, the rejection rule is satisfied, "yes" branch of block 134. The pending VT or VF detection based on the NID being reached at block 132 is withheld at block 140, and no anti-tachyarrhythmia therapy is delivered.

If all rejection rules are not satisfied, "no" branch of block 134, the pending detection of the VT or VF episode is not withheld. VT or VF is detected at block 136 based on the respective VT or VF interval counter reaching a corresponding NID. Control circuit 80 controls therapy delivery circuit 84 to deliver an appropriate anti-tachyarrhythmia therapy, e.g., ATP or a cardioversion/defibrillation shock, according to programmed therapy control parameters.

Figures 8, 9:
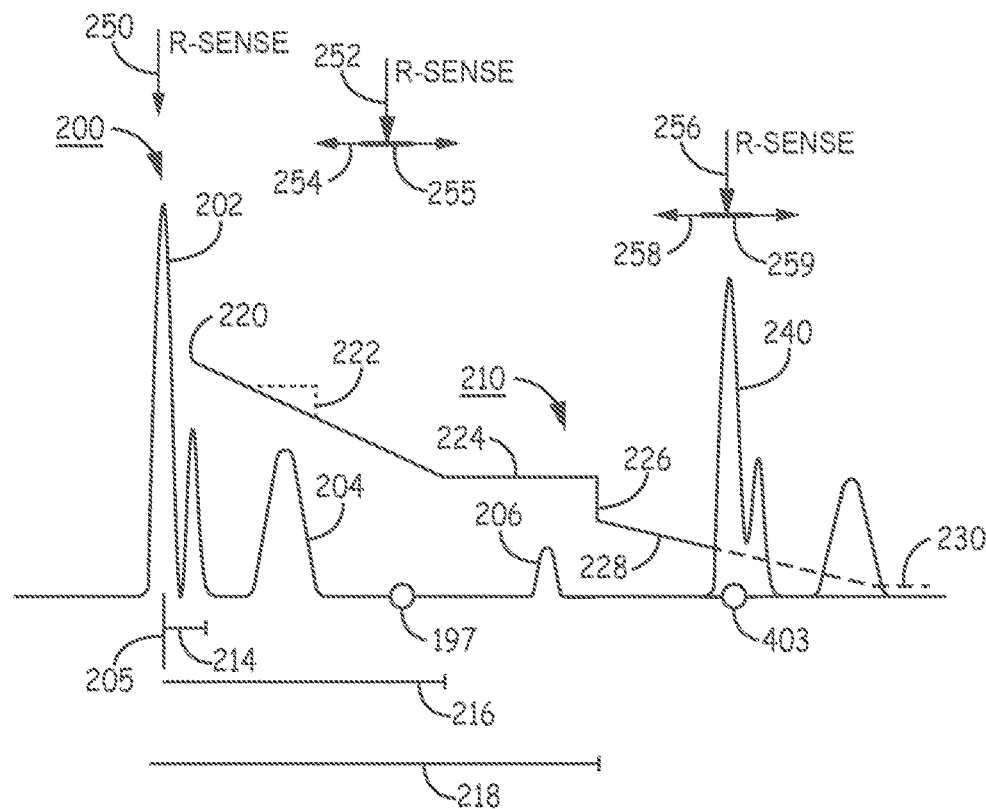
FIG. 8 is a diagram of a filtered cardiac electrical signal and an amplitude ratio threshold that may be applied for confirming R-wave sensed events.
FIG. 9 is an example of a look-up table of amplitude ratio threshold values that may be stored in memory of the ICD of FIGS. 1A-2C for use in confirming R-wave sensed events.

FIG. 8 is a diagram of a filtered, second cardiac electrical signal 200 and an amplitude ratio threshold 210 that may be applied to the amplitude ratio determined from the second cardiac electrical signal at block 118 of FIG. 7 for confirming an R-wave sensed event signal from the first sensing channel 83. The amplitude ratio is not a sensing threshold that is compared to the second cardiac electrical signal 200 in real time. The first sensing channel 83 may operate by sensing an R-wave when the first cardiac electrical signal crosses an R-wave amplitude sensing threshold defined in mV. The second cardiac electrical signal provided to control circuit 80 by the second sensing channel 85, however, is not compared to an amplitude sensing threshold in real time as it is acquired. Rather, as described in conjunction with FIG. 7, if the first sensing channel 83 produces an R-wave sensed event signal, the second cardiac electrical signal is buffered in memory 82 and if a tachyarrhythmia interval counter reaches an R-wave confirmation threshold, the buffered signal is post-processed to determine if the ratio of a maximum amplitude determined from the buffered signal segment to the maximum amplitude determined from a preceding confirmed R-wave of the second cardiac electrical signal reaches or exceeds the ratio threshold 210.

The ratio threshold 210 is shown relative to the second cardiac electrical signal 200 because the ratio threshold 210 is not a fixed value but varies over time. Ratio threshold 210 decreases as the time since the confirmed R-wave 202 increases. This time-variant ratio threshold is why the control circuit 80 determines the time since the preceding confirmed R-wave sensed event at block 120 of FIG. 7 in order to determine the value of the ratio threshold at block 122 that is applied to the amplitude ratio for confirming or not confirming the R-wave sensed event signal.

Cardiac electrical signal 200 may be produced by the second sensing channel 85 by filtering, amplifying and digitizing the cardiac electrical signal received by the second sensing electrode vector. While signal 200 is shown conceptually as having only positive-going waveforms it is to be understood that signal 200 may have positive- and negative-going portions and need not be a rectified signal. The absolute value of the maximum peak amplitude, positive or negative, may be determined from the stored second cardiac electrical signal segment at block 116 of FIG. 7. Cardiac electrical signal 200 includes an R-wave 202, a T-wave 204, a P-wave 206, and a subsequent R-wave 240. R-wave 202 represents a confirmed event occurring at time point 205. Time point 205 is the sample point of the maximum absolute value of the differential signal determined in response to an R-wave sense event signal 250 as described above in conjunction with FIG. 7.

If an R-wave sensed event signal occurs during a blanking interval 214 following time point 205 of a preceding confirmed R-wave 202, the new R-wave sensed event is not confirmed. Sensing channel 83 may have sensed the same R-wave 202 twice or sensed non-cardiac electrical noise as an R-wave.

After the blanking interval, the ratio threshold 210, at a time point corresponding to the expiration of blanking interval 214, is equal to a starting value 220 which may be set to 0.6 in one example, but may range between 0.4 and 0.7 in other examples. In one implementation, the ratio threshold 210 is stored in a look-up table and retrieved from memory 82 by control circuit 80 for comparison to an amplitude ratio determined in response to an R-wave sensed event signal from the first sensing channel.

FIG. 9 is an example of a look-up table 300 of ratio threshold values 304 that may be stored in memory 82 for respective event time intervals, which may be stored as corresponding sample point numbers 302. If the blanking interval 214 is approximately 150 ms, the first sample point at which a maximum amplitude may be determined as an event time point is at sample point 38 when the sampling rate is 256 Hz. In other examples, blanking interval 214 may be longer or shorter than 150 ms and the first sample point number stored in look-up table 300 will correspond to the sample point number at which the blanking interval 214 expires after the confirmed event time point 205, considered to "zero" sample point.

The ratio threshold is stored for the first sample point number entry as being the starting ratio threshold value 220, which is 0.6 in this example. If the control circuit 80 receives an R-wave sensed event signal from the first sensing channel 83, and a detection interval counter is equal to or greater than the R-wave confirmation threshold, a maximum event amplitude and event time is determined from the buffered, second cardiac electrical signal. The event time may be determined as the sample point number since the event time 205 of the most recent confirmed R-wave 202. If the event time is determined to be sample point number 38, control circuit 80 retrieves the ratio threshold, 0.6 in this example, stored in the look-up table 300 for the sample point number 38. This ratio threshold value is applied to the amplitude ratio determined from the maximum amplitude of the buffered, second cardiac electrical signal to the maximum amplitude determined from the most recent confirmed R-wave 202.

Referring again to FIG. 8, the ratio threshold 210 is shown to decrease at a constant decay rate 222 until the expiration of a first time interval 216. Time interval 216 may be defined to start at the time point 205 of the confirmed event 202 or start upon expiration of blanking interval 205. Time interval 216 may extend for up to 1 second from the time point 205 of the most recent confirmed R-wave 202. The decay rate 222 may, in one example, be approximately 0.3/second so that if time interval 216 is approximately 1 second, ratio threshold value 224 is 0.3 when the starting ratio threshold value 220 is 0.6.

Beginning at the expiration of time interval 216, ratio threshold 210 is held at a constant value 224 until a second time interval 218 expires. The constant value 224 is a ratio of approximately 1/3 (0.3) in one example but may be between 1/5 (0.2) and 1/2 (0.5) in other examples. Value 224 may be held for up to 500 ms after time interval 216 expires (for a total time interval 218 of up to 1.5 seconds). This change from the decay rate 222 to the constant value 224 is reflected in look-up table 300 as the ratio threshold 0.3 starting at sample point number 256 extending through sample point number 383.

At the expiration of time interval 218, the ratio threshold 210 drops stepwise to an intermediate ratio threshold value 226 then decays at a constant rate 228 until it reaches a minimum ratio threshold 230. The step drop from constant value 224 may be a drop to a ratio threshold of approximately 1/6 to 1/4. In one example, the ratio threshold drops from approximately 1/3 (0.3) to an intermediate ratio threshold of 1/5 (0.2) at 0.5 seconds after the expiration of time interval 216. This change is reflected in look-up table 300 as the ratio threshold of 0.2 at sample point 384 (0.5 seconds after sample point 256).

The second decay rate 228 may be the same as decay rate 222 or a slower decay rate such that ratio threshold 210 reaches the minimum ratio threshold 230, e.g., 1/32 (0.03), 1/64 (0.015) or other predetermined minimum ratio, approximately 2.5 seconds (sample point number 640) after the time point 205 of the preceding confirmed R-wave 202. The behavior of ratio threshold 210 moving forward in time from confirmed R-wave 202 is captured in look-up table 300 (FIG. 9). For example, at the example decay rate 222 of 0.3/second, the ratio threshold is 0.587 at sample point number 48, and so on.

The values recited here and reflected in look-up table 300 for ratio threshold values 220, 224, and 226 and 230 and time intervals 216 and 218 are illustrative in nature; other values less than or greater than the recited values may be used to implement a time-varying ratio amplitude for use in confirming an R-wave sensed event. The values for the ratio thresholds and time intervals used to control changes from one ratio threshold value to another or a decay rate and total decay interval will depend in part on the sampling rate, which is 256 Hz in the examples provided but may be greater than or less than 256 Hz in other examples.

Referring again to FIG. 8, if an R-wave sensed event signal 252 is produced by first sensing channel 83, control circuit 80 is triggered to store a time segment 254 of the second cardiac electrical signal 200 in memory 80. Time segment 254 may be 360 ms in one example, and may be between 300 ms and 500 ms in other examples. If a VT or VF or combined VT/VF interval counter has reached an R-wave confirmation threshold, control circuit 80 determines a maximum amplitude from the buffered cardiac signal time segment. As described above, the maximum amplitude may be the maximum absolute value of an x-order differential signal determined from the second cardiac electrical signal 200. The maximum amplitude may be determined from a portion of the stored cardiac signal time segment. For example, the maximum amplitude may be determined from a segment 255 that is a sub-segment or portion of the stored time segment 254. Segment 255 may be approximately 50 to 300 ms long, e.g., 200 ms long, when the total time segment 254 is 360 ms to 500 ms long. The segment 255 may be defined relative to the time the R-wave sensed event signal 252 is received.

The sample point number 197 at which the maximum amplitude within the time segment 255 occurs represents the number of sample points since the event time 205 (sample point number zero) of the most recent confirmed R-wave 202. The sample point number 197 is determined as the event time of the maximum amplitude of cardiac signal time segment 255. Control circuit 80 uses this sample point number to look up the corresponding ratio threshold 304 in look-up table 300. For the sake of example, the maximum amplitude during time segment 255 obtained in response to R-wave sensed event signal 252 may occur at sample point number 197 approximately 0.77 seconds after event time point 205. The stored ratio threshold for sample point number 197 may be approximately 0.4 for a decay rate 222 of approximately 0.3/second (or 0.0012 per sample point) from the starting value 220, which is 0.6 beginning at sample point number 38 in this example. If the amplitude ratio of the maximum amplitude determined at sample point number 197 during time segment 255 to the maximum amplitude determined for confirmed R-wave 202 is greater than or equal to 0.4, R-wave sensed event 252 is confirmed. In this example, the cardiac electrical signal has a low, baseline amplitude during interval 255, and as such the R-wave sensed event signal 252 is not confirmed. Control circuit 80 increases the unconfirmed event counter as described in conjunction with FIG. 7.

Similarly, control circuit 80 may receive R-wave sensed event signal 256 and determine a maximum amplitude during time segment 259, defined relative to R-wave sensed event signal 256, of the buffered cardiac electrical signal segment 258. The event time sample point number 403 at which the maximum amplitude occurs since event time 205 is used to look up the ratio threshold from look up table 300. In this case, the amplitude ratio determined from the buffered, second cardiac electrical signal during time segment 259 exceeds the ratio threshold 210 at the event time sample point number 403 of the maximum amplitude during time segment 259, which corresponds to R-wave 240. R-wave sensed event signal 256 is confirmed by control circuit 80. In this way, the second cardiac electrical signal from sensing channel 85 is analyzed only when an R-wave sensed event confirmation condition is met, e.g., a tachyarrhythmia interval counter is active and has reached a threshold count, which may be less than a required number of intervals to detect a VT or VF episode. The R-wave sensed event of the first sensing channel is confirmed based on post-processing of the buffered, second cardiac electrical signal.

Figure 10:
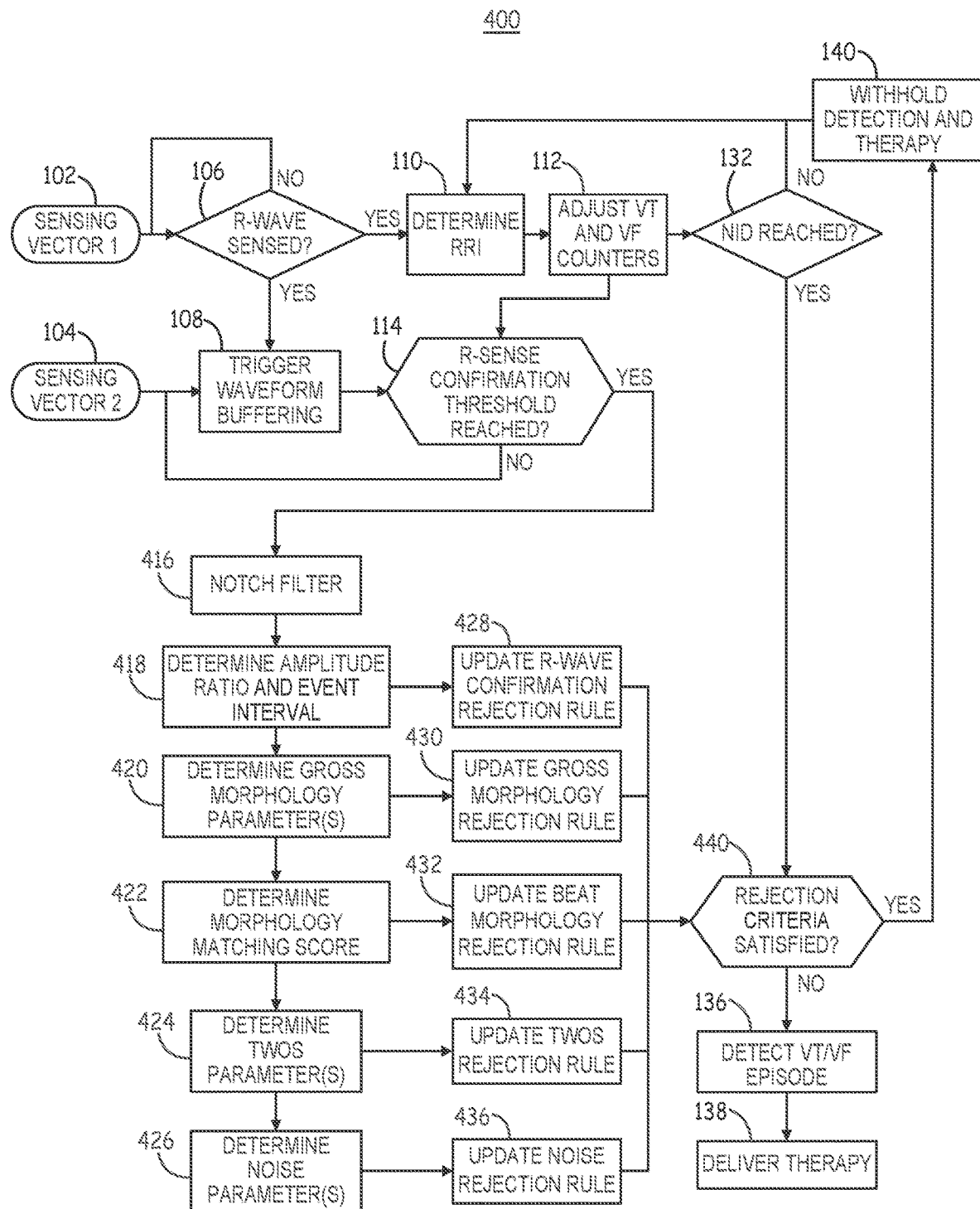
FIG. 10 is a flow chart of a method for detecting tachyarrhythmia by an ICD according to one example.

FIG. 10 is a flow chart 400 of a method for detecting tachyarrhythmia by ICD 14 according to another example. Operations performed at blocks 102-114, 132, 136, 138 and 140 in flow chart 400 may generally correspond to identically-numbered blocks shown in FIG. 7 and described above. At blocks 102 and 104, two different sensing electrode vectors are selected by sensing circuit 86 for receiving a first cardiac electrical signal by first sensing channel 83 and a second cardiac electrical signal by second sensing channel 85 as described above in conjunction with FIGS. 5 and 7.

Sensing circuit 86 may produce an R-wave sensed event signal at block 106 in response to the first sensing channel 83 detecting an R-wave sensing threshold crossing by the first cardiac electrical signal. The R-wave sensed event signal may be passed to control circuit 80. In response to the R-wave sensed event signal, control circuit 80 is triggered at block 108 to store a segment of the second cardiac electrical signal received from the second sensing channel 85 in a circulating buffer of memory 82. A digitized segment of the second cardiac electrical signal, which may be defined in time relative to the time of the R-wave sensed event signal received from sensing circuit 86, and may be 100 to 500 ms long, for example. In one example, the buffered segment of the cardiac electrical signal is at least 92 sample points obtained at a sampling rate of 256 Hz, or approximately 360 ms, of which 68 sample points may precede and include the sample point at which the R-wave sensed event signal was received and 24 sample points may extend after the sample point at which the R-wave sensed event signal was received.

In addition to buffering a segment of the second cardiac electrical signal, control circuit 80 responds to the R-wave sensed event signal produced at block 106 by determining an RRI at block 110 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia detection counters at block 112 as described above in conjunction with FIG. 7.

After updating the VT and VF interval counters at block 112, tachyarrhythmia detector 92 compares the interval counter values to an R-sense confirmation threshold at block 114 and to VT and VF NID detection thresholds at block 132. If a VT or VF interval counter has reached an R-sense confirmation threshold, "yes" branch of block 114, the second cardiac electrical signal from sensing channel 85 is analyzed to confirm the R-wave sensed at block 106 by the first sensing channel 83. The R-sense confirmation threshold is a count of two on the VT interval counter and a count of 3 on the VF interval counter in one example. Other examples are given above in conjunction with FIG. 7.

If the R-sense confirmation threshold is not reached by any of the interval counters at block 114, the control circuit 80 waits for the next R-wave sensed event signal at block 108 to buffer the next segment of the second cardiac electrical signal. In some cases, the oldest buffered cardiac signal segment may be overwritten by the next cardiac signal segment without ever being analyzed for confirming an R-wave, or analyzed for any other purpose, since analysis of the buffered cardiac signal segment is not required if the VT and VF interval counters are inactive (at a count of zero) or remain below the R-sense confirmation threshold.

If an R-sense confirmation threshold is reached at block 114, the control circuit 80 applies a notch filter to the stored, second cardiac electrical signal segment at block 416. The notch filter applied at block 416 may correspond to the filter described in conjunction with FIG. 6. The notch filter significantly attenuates 50-60 Hz electrical noise, muscle noise, other EMI, and other noise/artifacts in the stored, second cardiac electrical signal segment. Using the notch filtered segment, control circuit 80 performs multiple analyses on the segment to determine if any rejection rules are satisfied. As described below, if a rejection rule is satisfied, a pending VT or VF episode detection made based on an NID threshold being reached at block 132 may be withheld.

As described in conjunction with FIG. 7, an amplitude ratio may be determined at block 418 for confirming the R-wave sensed event signal that triggered the buffering of the currently stored, second cardiac electrical signal segment. Determinations made at block 418 may include the operations performed at blocks 116, 118 and 120 of FIG. 7. The amplitude ratio is used to update an R-wave confirmation rejection rule at block 428.

The maximum peak amplitude used to determine the amplitude ratio may be determined from a portion of the stored cardiac signal segment at block 418. For example, if a 360 ms or 500 ms segment is stored at block 108, only a 200 ms segment, e.g., approximately 52 sample points sampled at 256 Hz, which may be centered in time on the R-wave sensed event signal may be analyzed for determining the amplitude ratio at block 418. A longer signal segment may be stored at block 108 than required for determining the amplitude ratio at block 418 so that a longer segment is available for other signal analysis procedures performed by tachyarrhythmia detector 92 as described below, e.g., for determining a morphology match score for detecting TWOS as described in conjunction with FIGS. 14 through 16.

Control circuit 80 may determine an event interval at block 418 as the time interval or number of sample points from the maximum peak amplitude to the preceding confirmed R-wave sensed event, when the current R-wave sensed event signal is not the first one being confirmed since the R-sense confirmation threshold was reached at block 114. At block 428, control circuit 80 may compare the amplitude ratio to a ratio threshold, which may be retrieved from a look-up table stored in memory 82 using the determined event interval as described in conjunction with FIGS. 8 and 9. If the amplitude ratio is greater than the ratio threshold, the sensed R-wave is confirmed. If the amplitude ratio is less than the ratio threshold, the sensed R-wave is not confirmed.

An X of Y unconfirmed beat counter may be updated by tachyarrhythmia detector 92 at block 428 to reflect the number of R-wave sensed event signals that are not confirmed out of the most recent Y R-wave sensed event signals. For example, the X of Y counter may count how many R-waves are not confirmed to be R-waves out of the most recent 12 R-wave sensed event signals. If the X of Y count reaches a rejection threshold, e.g., if at least 3, 4, 5 or another predetermined number out of 12 R-wave sensed event signals are not confirmed to be R-waves, the R-wave rejection rule for withholding tachyarrhythmia detection is satisfied. A flag or logic value may set by control circuit 80 to indicate the R-wave rejection rule is satisfied. Updating the R-wave rejection rule at block 428 may include operations described in conjunction with FIG. 7 for blocks 122, 124, 126, 128, 130 and 134.

At blocks 420, 422, 424 and 426, other cardiac signal parameters may be determined from the notch-filtered, cardiac signal segment for updating the status of other tachyarrhythmia detection rejection rules at respective blocks 430, 432, 434 and 436. In some examples, a digitized cardiac electrical signal from first sensing channel 83 may be analyzed and used in updating the status of a tachyarrhythmia detection withhold rule. For example, the notch filtered, cardiac electrical signal from the second sensing channel 85 may be analyzed at blocks 420, 422 and 426 for updating a gross morphology rejection rule, a beat morphology rejection rule and a noise rejection rule at blocks 430, 432, and 436, respectively. The differential signal 69 (see FIG. 5) from the first sensing channel 83 may be analyzed at block 424 for updating the T-wave oversensing (TWOS) rule at block 434.

At block 420 one or more gross morphology parameters are determined from the notch-filtered, second cardiac signal segment. Gross morphology parameters may include, but are not limited to, a low slope content, a noise pulse count, a normalized rectified amplitude or other noise metrics. Examples of gross morphology parameters that may be determined are generally disclosed in the above-incorporated U.S. Pat. No. 7,761,150 (Ghanem, et al.) and U.S. Pat. No. 8,437,842 (Zhang, et al.). The gross morphology parameters may be determined using the entire second cardiac signal segment stored at block 108 or a portion of the stored segment. In one example, at least 92 sample points, approximately 360 ms, are analyzed for determining the gross morphology parameters, which may be a portion of or the entire stored segment.

The gross morphology parameters are used at block 430 to update the status of a gross morphology rejection rule. Criteria or thresholds may be applied to each gross morphology parameter determined, and the gross morphology rejection rule may be satisfied when a required number of the gross morphology parameters meet the criteria or threshold applied to the respective parameter. For example, if at least two out of three gross morphology parameters satisfy noise detection criteria, the gross morphology rejection rule is satisfied. Control circuit 80 may set a flag or logic signal indicating so at block 430.

At block 422 a morphology matching score is determined from the stored, second cardiac electrical signal segment. The morphology matching score may be determined by performing wavelet transform or other morphology matching analysis on a portion of the stored segment, e.g., on at least 48 signal sample points or about 190 ms, and may be performed using the notch filtered signal produced at block 416. The morphology matching analysis may include aligning a selected portion of the stored segment with a previously-determined known R-wave template and determining a morphology matching score. The morphology matching score may have a possible range of values from 0 to 100 and indicates how well the morphology of the second cardiac signal segment matches the known R-wave template. A wavelet transform method as generally disclosed in U.S. Pat. No. 6,393,316 (Gillberg et al.) is one example of a morphology matching method that may be performed at block 422 for determining a matching score. Other morphology matching methods that may be implemented by tachyarrhythmia detector 92 may compare the wave shape, amplitudes, slopes, inflection time points, number of peaks, or other features of the stored second cardiac electrical signal to a known R-wave template. More specifically, waveform duration or width, waveform polarity, waveform positive-going slope, waveform negative-going slope, and/or other waveform features may be used alone or in combination to characterize the similarity between the unknown waveform and a known R-wave template. Morphology matching methods may use one or a combination of two or more morphology features of the stored second cardiac electrical signal for determining a match to a known R-wave template. A posture-independent method for determining a morphology match score may be performed that includes generating posture-independent R-wave templates for use in template matching as generally disclosed in pre-grant U.S. Pat. Publication No. 2016/0022166 (Stadler, et al.), incorporated herein by reference in its entirety. Other beat morphology matching techniques that may be used at block 422 are generally disclosed in U.S. Pat. No. 8,825,145 (Zhang, et al.) and U.S. Pat. No. 8,983,586 (Zhang et al.), both incorporated herein by reference in their entirety.

The morphology matching score is used at block 432 by tachyarrhythmia detector 92 to update a beat morphology rejection rule. The beat morphology rejection rule may be satisfied when a minimum number of morphology match scores out of a predetermined number of most recent morphology match scores exceed a match score threshold in one example. For example, if at least three out of 8 of the most recent morphology match scores exceed a match score threshold of 50, 60, 70 or other score threshold, the beat morphology rejection rule is satisfied. A relatively high match score, exceeding a selected match score threshold, indicates the unknown beat matches the known R-wave template and is therefore a normal R-wave rather than a VT or VF beat. As such, when a threshold number of the most recent morphology match scores are determined to be normal R-waves, the beat morphology rejection rule is satisfied, and control circuit 80 may set a flag or logic signal indicating so.

At block 424, TWOS parameters are determined from a stored, digitized cardiac electrical signal. In some cases, the TWOS parameters are determined from a first order differential signal 69 received from first sensing channel 83 as described in conjunction with FIG. 5 above and FIGS. 14 and 15 below. The first order differential signal is determined by subtracting the amplitude of the n−1 sample point from the nth sample point. Alternatively or additionally, the second cardiac electrical signal from sensing channel 85, before or after notch filtering, may be used for determining TWOS parameters for detecting TWOS based on morphology analysis of the stored cardiac signal, e.g., as described in conjunction with FIG. 16. Tachyarrhythmia detector 92 may be configured to execute TWOS rejection algorithms by determining a differential filtered cardiac electrical signal and TWOS parameters as generally disclosed in the above-incorporated U.S. Pat. No. 7,831,304 (Cao, et al). Other aspects of detecting TWOS that may be used for determining TWOS parameters from either the first and/or second cardiac electrical signal are generally disclosed in U.S. Pat. No. 8,886,296 (Patel, et al.) and U.S. Pat. No. 8,914,106 (Charlton, et al.), both incorporated herein by reference in their entirety.

At block 434, the TWOS parameter(s) determined for the currently stored cardiac signal segment are used by the tachyarrhythmia detector 92 to update the status of a TWOS rejection rule as being either satisfied or unsatisfied. For example, if one or more TWOS parameters indicate the R-wave sensed event signal produced by the first sensing channel 83 is likely to be an oversensed T-wave, a TWOS event counter may be updated at block 434. If the TWOS event counter reaches a threshold, the TWOS rejection rule is satisfied. Control circuit 80 may set a flag or logic signal indicating when the TWOS rejection rule is satisfied.

Other noise parameters may be determined at block 426 to identify oversensing due to noise artifacts. The noise parameters determined at block 426 may include determining peak amplitudes from the notch-filtered second cardiac electrical signal segment. All or a portion of the stored signal segment may be used for determining one or more amplitude peaks. The peak amplitudes determined at block 426 may include the maximum peak amplitude determined at block 418 for use in determining the amplitude ratio. The maximum peak amplitudes for one or more stored cardiac signal segments are compared to noise detection criteria for determining whether the noise rejection rule is satisfied at block 436. Control circuit 80 sets a flag or logic signal to indicate the status of the noise rejection rule at block 436.

After adjusting the VT and VF interval counters at block 112, the tachyarrhythmia detector 92 compares the interval counters to VT and VF NID detection thresholds at block 132. If the NID has been reached by either the VT or VF interval counter, tachyarrhythmia detector 92 checks the status of the rejection rules at block 440. If rejection criteria are satisfied at block 440, "yes" branch of block 440, based on the status of one or more rejection rules, the VT or VF detection based on RRI analysis at blocks 110, 112, and 132 is withheld at block 140. No VT or VF therapy is delivered. The process returns to block 110 to determine the next RRI upon receiving the next R-wave sensed event signal from sensing channel 83.

If the rejection criteria are not satisfied, "no" branch of block 440, the VT or VF episode is detected at block 136 according to which VT or VF interval counter reached its respective NID threshold. Control circuit 80 controls therapy delivery circuit 84 to deliver a therapy at block 138 according to the type of episode detected and programmed therapy delivery control parameters.

In some examples, the rejection criteria applied at block 440 require only a single rejection rule be satisfied in order to cause the tachyarrhythmia detector 92 to withhold a VT or VF detection. In other examples, two or more rejection rules may be required to be satisfied before an RRI-based VT or VF detection is withheld. In still other examples, one rejection rule may be linked with another rejection rule in order to have rejection criteria satisfied at block 440. For instance, the R-wave confirmation rejection rule may only be used to satisfy the rejection criteria when the gross morphology rejection rule is also satisfied. In this case, the R-wave confirmation rejection rule alone may not be used to satisfy the rejection criteria at block 440. The gross morphology rejection rule may be used only with the R-wave confirmation rejection rule, alone or in combination with another rule to satisfy the rejection criteria.

The rejection rules updated at blocks 428 through 436 may be programmably enabled or disabled by a user using external device 40. Control circuit 80 may determine which parameters are determined at blocks 418 through 426 as required for updating the status of only the rejection rules that are enabled or programmed "ON."

Figure 11:
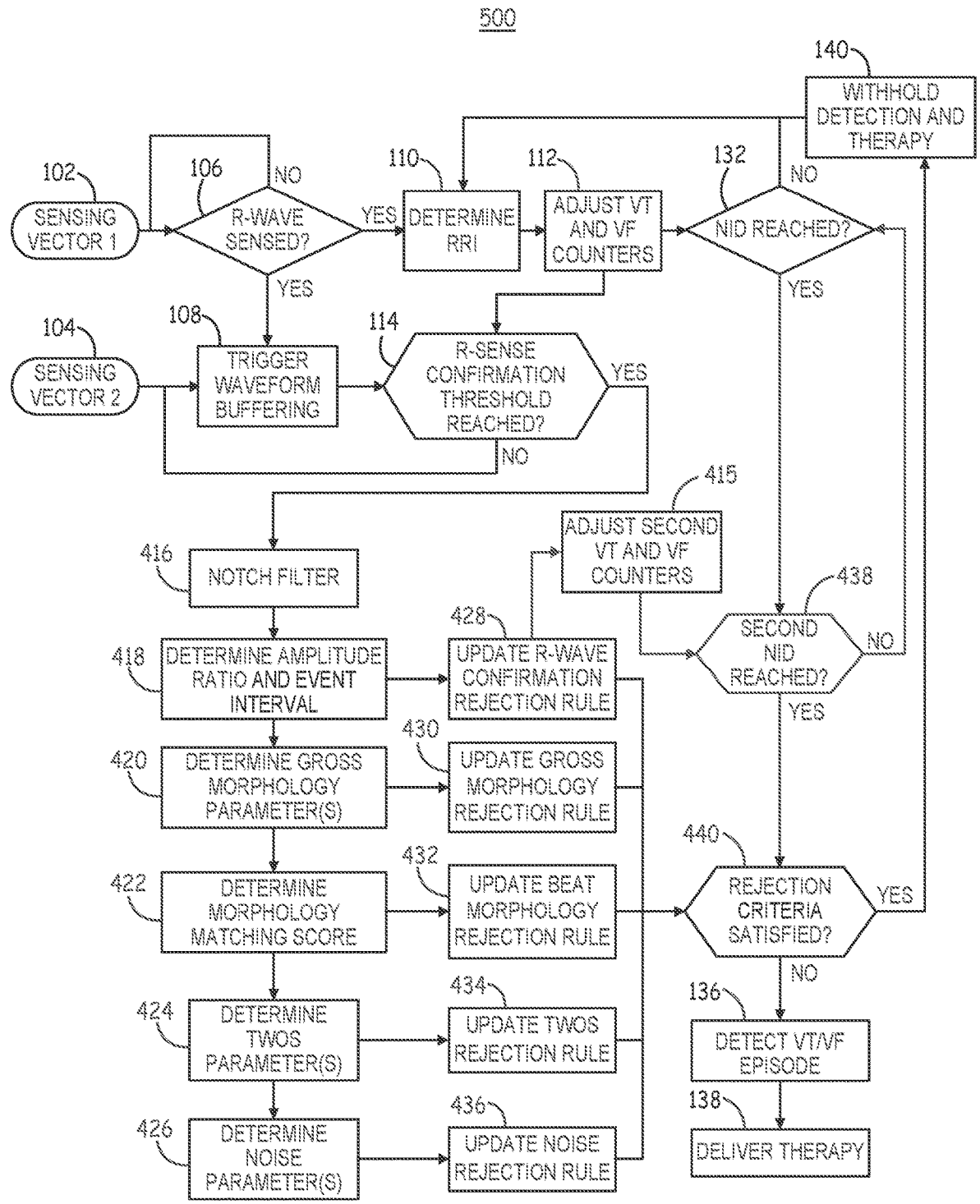
FIG. 11 is a flow chart of a method for detecting tachyarrhythmia by an ICD according to another example.

FIG. 11 is a flow chart 500 of a method for detecting tachyarrhythmia by ICD 14 according to another example. In the examples of FIG. 7 and FIG. 10, the number of RRIs determined from the first sensing electrode vector 102 that fall into a respective VT or VF interval range or zone are tracked by respective VT and VF interval counters. The counts of the VT and VF interval counters are compared to respective VT and VF NID thresholds at block 132. Identically-numbered blocks in FIG. 11 correspond to like-numbered blocks shown in FIGS. 7 and 10 as described above.

In other examples, the second cardiac electrical signal received by the second sensing channel 85 from the second electrode vector at block 104 may also be used for determining RRIs and determining whether an NID threshold is reached at decision block 438. Tachyarrhythmia detector 92 may include second VT and VF interval counters for counting RRIs determined from the second cardiac electrical signal received by the second sensing channel 85. The second VT and VF interval counters may be updated at block 415 based on RRIs determined from the second cardiac electrical signal received via the second sensing electrode vector 104.

In one instance, the tachyarrhythmia detector 92 may begin updating second VT and VF interval counters at block 415 after the R-sense confirmation threshold is reached at block 114. The process of updating the second VT and VF interval counters from an initialized zero count may include confirming an R-wave at block 428 based on comparing an amplitude ratio to a ratio threshold as described in conjunction with blocks 122, 124, 126, and 128 of FIG. 7. If the R-wave sense is confirmed at block 126, the R-wave confirmation rejection rule is updated at block 428 based on the confirmed R-wave sensed event, and tachyarrhythmia detector 92 compares the event interval determined at block 418 to VT and VF interval zones at block 415. The event interval determined at block 418 is the time interval from the most recently confirmed R-wave event time to the event time of the maximum absolute amplitude of the time segment stored for the most recent R-wave sensed event signal.

If the most recent R-wave sensed event signal is confirmed at block 428, the event interval may be compared at block 415 to VT and VF interval zones defined to be the same as the interval zones applied at block 112 to RRIs determined from R-wave sensed event signals produced by the first sensing channel 83. If the event interval determined at block 418 for a confirmed R-wave falls into the VT interval zone, the second VT interval counter is increased at block 415. If the event interval falls into the VF interval zone, the second VF interval counter is increased at block 415. In some examples, a combined VT/VF interval counter is increased if the event interval falls into either a VT or VF interval zone.

If one of the first VT or VF interval counters (or a combined VT/VF interval counter) applied to RRIs determined from the first sensing channel 83 reaches an NID at block 132, tachyarrhythmia detector 92 may compare the second VT and VF interval counters to second NID requirements at block 438. The second VT NID and the second VF NID used by tachyarrhythmia detector 92 may be less than the VT NID and VF NID applied to the first VT and VF interval counters at block 132. The second VT and VF interval counters begin to be updated after the R-sense confirmation threshold is reached at block 114 in some examples. As such, the second VT and VF interval counters may have counts that are less than the first VT and VF interval counters (that are adjusted at block 112). The counts of the second VT and VF interval counters may fall behind the first VT and VF interval counts by the number of intervals required to reach the R-sense confirmation threshold. For example, if a first VT interval counter is required to have a count of at least 2 or the first VF interval counter is required to have a count of at least 3 in order for the R-sense confirmation threshold to be reached at block 114, the second VT or VF interval counter may have a count that is at least 2 or 3, respectively, less than the first respective VT or VF interval counter.

If a second NID is reached by one of the second VT or VF interval counters, "yes" branch of block 438, tachyarrhythmia detector 92 determines if rejection criteria are met at block 440 based on the status of the rejection rules updated at block 428 through 436 as described above in conjunction with FIG. 10. If the second NID is not reached at block 438 by neither of the second VT or VF interval counters, "no" branch of block 438, tachyarrhythmia detector 92 does not advance to checking the rejection criteria at block 440. Rather, tachyarrhythmia detector 92 may wait for the first VT or VF NID to be reached at block 132 by the respective first VT or VF interval counter and for the respective second NID to be reached at block 438 by the respective second VT or VF interval counter. For instance, in order to advance to block 440 to determine if rejection criteria are satisfied and subsequently either detect VT at block 136 or withhold a VT detection at block 140, the first VT interval counter is required to reach the first VT NID at block 132 and the second VT interval counter is required to reach the second VT NID at block 438. Similarly, in order to advance to block 440 to determine if rejection criteria are satisfied and subsequently either detect VF at block 136 or withhold a VF detection at block 140, the first VF interval counter is required to reach the first VF NID at block 132 and the second VF interval counter is required to reach the second VF NID at block 438.

Figure 12:
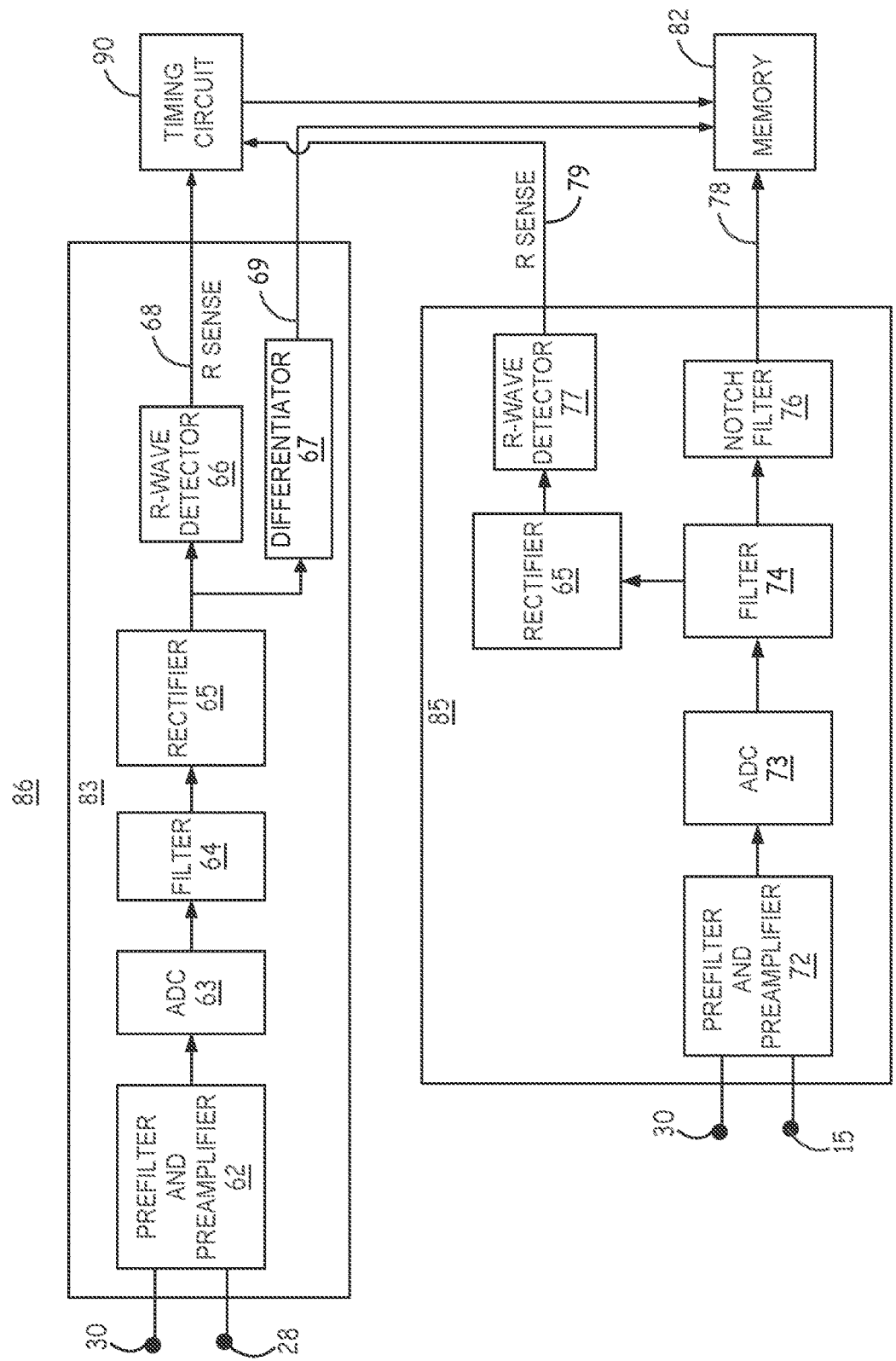
FIG. 12 is a diagram of circuitry included in the sensing circuit of FIG. 4 according to another example.

FIG. 12 is a diagram of circuitry included in the sensing circuit of FIG. 4 according to another example. In FIG. 12, identically-numbered components of sensing channels 83 and 85 correspond to like-numbered components described in conjunction with and shown in FIG. 5. In the example of FIG. 5, first sensing channel 83 is configured to sense R-waves by R-wave detector 66 in real time and produce R-wave sensed event signals 68 that are passed to timing circuit 90 as the R-waves are sensed. Second sensing channel 85 is configured to pass the filtered, digitized output signal 78 to memory 82 for storage of second cardiac electrical signal segments as triggered by R-wave sensed event signals 68 from first sensing channel 83 without performing real-time R-wave sensing from the second cardiac electrical signal.

In the example of FIG. 12, second sensing channel 85 is configured to pass the digitized filtered output signal 78 to memory 82 for storage of second cardiac electrical signal segments as described above. Sensing channel 85 is additionally configured to perform real-time R-wave sensing from the second cardiac electrical signal. In this case, second sensing channel 85 includes rectifier 75 for rectifying the digitized and bandpass filtered signal output of filter 74. The rectified signal is passed from rectifier 75 to R-wave detector 77. R-wave detector may include a sense amplifier, comparator or other R-wave detection circuitry configured to apply an auto-adjusting R-wave sensing threshold to the rectified signal for sensing an R-wave in response to a positive-going R-wave sensing threshold crossing.

Second sensing channel 85 may produce R-wave sensed event signals 79 that are passed to timing circuit 90 in real time for use in determining RRIs based on the second cardiac electrical signal. RRIs may be determined as the time interval or sample point count between consecutively received R-wave sensed event signals 79. Timing circuit 90 may pass RRIs determined from R-wave sensed event signals 79 from second sensing channel 85 to tachyarrhythmia detector 92 for use in updating second VT and VF interval counters based on RRIs determined from real-time sensing of R-waves by the second sensing channel 85.

In the flow chart 500 of FIG. 11, second VT and VF interval counters are updated at block 415 by tachyarrhythmia detector 92 based on R-waves confirmed at block 428 as a result of post-processing of the stored second cardiac electrical signal segments. R-waves are not sensed by the second sensing channel 85 in real time in the example of FIG. 11 (the signal segments may be recorded but R-wave sense event signals are not produced in real time as R-waves are sensed based on an R-wave sensing threshold). In FIG. 12, the second sensing channel 85 is configured to sense R-waves in real time from the second cardiac electrical signal received by the second sensing vector 104, and, as such, tachyarrhythmia detector 92 may update second VT and VF interval counters based on real-time sensing of R-waves by the second sensing channel 85.

Figure 13:
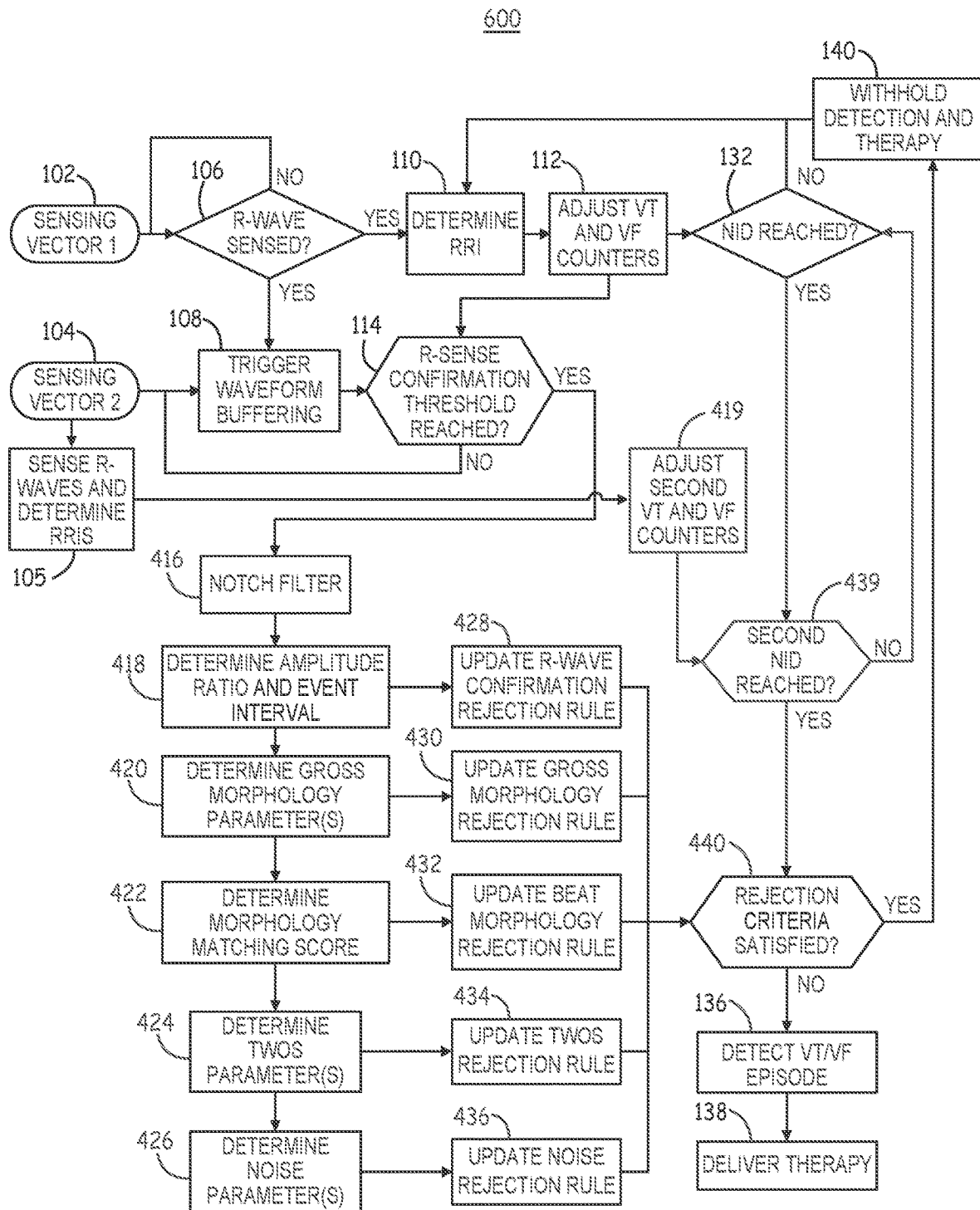
FIG. 13 is a flow chart of a method for detecting tachyarrhythmia by an ICD according to yet another example.

FIG. 13 is a flow chart 550 of a method for detecting tachyarrhythmia by ICD 14 according to another example in which the second sensing channel 85 is configured for real-time sensing of R-waves from the second cardiac electrical signal in addition to the control circuit 80 being configured to confirm R-waves sensed by the first sensing channel 83 by post-processing of the second cardiac electrical signal. Identically-numbered blocks in FIG. 13 correspond to like-numbered blocks shown in FIGS. 7 and/or 11 and described in conjunction therewith.

In the example of FIG. 13, at block 105, R-wave detector 77 of sensing channel 85 produces R-wave sensed event signals 79 (shown in FIG. 12), e.g., in response to crossings of a second R-wave sensing threshold by the second cardiac electrical signal. The second R-wave sensing threshold may be an auto-adjusting threshold and may be different than the R-wave sensing threshold used by R-wave detector 66 of the first sensing channel 83. Timing circuit 90 determines RRIs between consecutive R-wave sensed event signals 79 received from second sensing channel 85 at block 105 and passes the determined RRIs to tachyarrhythmia detector 92. At block 419, tachyarrhythmia detector 92 adjusts the second VT interval counter or the second VF interval counter, which may both be X of Y type counters, in response to each RRI determined at block 105. In this example, the second VT and VF interval counters of tachyarrhythmia detector 92 may be updated in real time, similar to the first VT and VF interval counters used to count RRIs determined from the first cardiac electrical signal. The second VT and VF interval counters may be updated on a beat-by-beat basis without requiring the R-sense confirmation threshold to be reached first (block 114).

If the tachyarrhythmia detector 92 determines that a first VT NID or first VF NID is reached at block 132, the tachyarrhythmia detector 92 compares the second VT and VF interval counters to a second VT NID and second VF NID, respectively, at block 439. In this case, the second VT NID and second VF NID may be the same as the first VT NID and the first VF NID since all of the first and second VT interval counters and the first and second VF interval counters are being updated in response to R-waves that are sensed in real time. If the second VT or VF NID has not been reached ("no" branch of block 430), the tachyarrhythmia detector 92 may return to block 132 to wait for the VT or VF NID thresholds to be reached based on R-waves sensed in real time by both the respective first and second sensing channels 83 and 85.

If a second VT or VF NID is reached at block 439 when a corresponding first VT or VF NID is reached at block 132, the tachyarrhythmia detector 92 determines if rejection criteria are satisfied at block 440 as described previously in conjunction with FIG. 10. A pending VT of VF detection based on tachyarrhythmia intervals being detected in real time from both the first and second cardiac electrical signals is either withheld at block 140 in response to rejection criteria being met or the VT or VF detection is confirmed at block 135 if the rejection criteria are not satisfied. Control circuit 80 controls the therapy delivery circuit to deliver an anti-tachyarrhythmia therapy at block 138 in response to the VT or VF detection.

Figure 14:
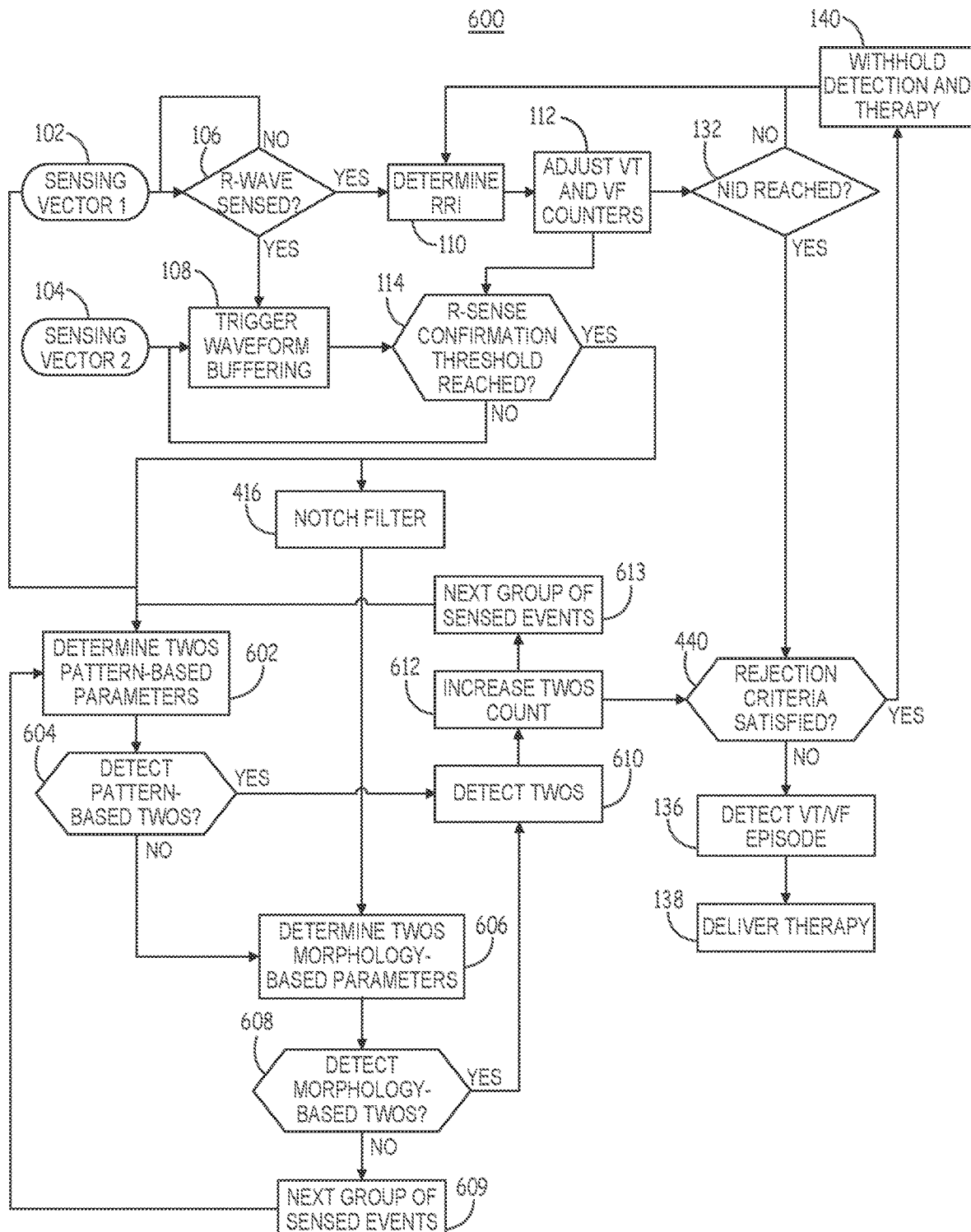
FIG. 14 is a flow chart of a method performed by an ICD for rejecting an RRI-based VT or VF detection in response to a T-wave oversensing (TWOS) rejection rule being satisfied.

FIG. 14 is a flow chart 600 of a method performed by ICD 14 for rejecting an interval-based VT or VF detection in response to the TWOS rejection rule of block 434 FIGS. 10, 11 and 13 being satisfied. Blocks 102 through 114, 132, 136, 138, and 140 of FIG. 14 correspond to identically-numbered blocks described above in conjunction with FIGS. 10, 11 and 13.

As described above, if the R-sense confirmation threshold is reached at block 114, the control circuit 80 applies a notch filter to the stored, second cardiac electrical signal segment at block 416. The notch filter applied at block 416 may correspond to the filter described in conjunction with FIG. 6. The notch-filtered, second cardiac electrical signal segments are used at blocks 606 and 608 for detecting TWOS based on morphological analysis of the stored second cardiac electrical signal segments. When the R-sense confirmation threshold is reached at block 114, the first cardiac electrical signal (from sensing vector 1, block 102) may also be used for detecting TWOS at blocks 602 and 604 based on sensed event patterns. In one example amplitude pattern-based TWOS parameters are determined at block 602 using the first cardiac electrical signal and signal morphology-based TWOS parameters are determined at block 606 using the notch-filtered, second cardiac electrical signal. The methods performed at blocks 602 and 606 for determining TWOS parameters may correspond to block 424 of FIGS. 10, 11, and 13.

At block 602, pattern-based parameters are determined by classifying sensed events based on an amplitude threshold. As described below in conjunction with FIG. 15, each event sensed by the first sensing channel 83 is classified as being either an R-wave or a T-wave based on an amplitude threshold. For example, when the R-sense confirmation threshold is reached, a group of six consecutively sensed events may be identified based on R-wave sensed event signals received from sensing circuit 86. An amplitude threshold may be determined based on the peak amplitudes of the differential signal 69 (FIG. 5) corresponding to the six consecutively sensed events. Each sensed event is classified as a T-wave if the differential peak amplitude is less than the amplitude threshold or classified as an R-wave if the differential peak amplitude is greater than the amplitude threshold. Methods for determining an amplitude threshold and classifying sensed events as T-waves or R-waves using a differential signal are generally disclosed in the above-incorporated U.S. Pat. No. 7,831,304 (Cao, et al.).

At block 604 an analysis of the pattern of the classified sensed events is performed to determine if a TWOS pattern is present. For example, a group of a predetermined number of consecutive sensed events may be identified. If at least two events of the group of sensed events, e.g., of a group of six sensed events, are classified as T-waves and each follows an immediately preceding event classified as an R-wave (forming an R-T pair), pattern-based evidence of TWOS is detected at block 610. Additional examples for detecting pattern-based TWOS at block 604 based on event classifications are given below in conjunction with FIG. 15.

At block 606, morphology-based parameters for detecting TWOS are determined from the notch-filtered second cardiac electrical signal. The morphology-based parameters may be determined at block 606 simultaneously with the determination of the pattern-based parameters determined at block 602. In other examples, the morphology-based parameters are determined at block 606 only if a pattern of TWOS is not detected at block 604 based on the analysis of classified sensed events. A morphology match score may be determined for each sensed event in the group of sensed events analyzed at block 602 and 604. The morphology match score is determined from the second cardiac electrical signal segments buffered at block 108 for each of event of the group of sensed events. The morphology match score may be based on a comparison of the waveform of the notch-filtered stored signal segment to a previously established normal R-wave template, e.g., using wavelet transform or other morphology matching techniques.

At block 608, control circuit 80 determines whether morphology-based evidence of TWOS is detected. An analysis of the morphology match scores determined at block 606 may be performed at block 608 to identify likely pairs of R-T events or pairs of T-R events as evidence of TWOS. Examples of methods for morphology-based parameter determination performed by control circuit 80 at block 606 and the analysis performed at block 608 to detect TWOS are described below in conjunction with FIG. 16.

In the example of FIG. 14, if TWOS is detected from the pattern-based analysis of the group of sensed events performed at block 604 or if TWOS is detected from the morphology-based analysis of the group of sensed events performed at block 608, TWOS is detected at block 610. If a group of six sensed events (or other predetermined number) is detected as TWOS based on either one of the pattern-based criteria applied at block 604 or the morphology-based criteria applied at block 608, the group of six sensed events causes the TWOS count to be increased by one at block 612. In other examples, both the pattern-based TWOS criteria applied at block 604 and the morphology-based TWOS criteria applied at block 608 may be required to be satisfied for detecting TWOS at block 610. If TWOS is detected at block 610, a TWOS count is increased by control circuit 80 at block 612. Control circuit 80 tracks the number of times TWOS is detected based on the analysis of a group of consecutive sensed events, e.g., a group of six consecutive sensed events.

In other examples, two separate TWOS counters may be included in control circuit 80 for separately counting the number of groups of consecutive sensed events satisfying the pattern-based TWOS criteria at block 604 and the number of groups of consecutive sensed events satisfying the morphology-based TWOS criteria at block 608. One TWOS counter is updated at block 612 when pattern-based TWOS is detected at block 604, and a second TWOS counter is updated at block 612 when TWOS is detected at block 608. In this case, rather than a "no" branch from block 604, the control circuit 80 advances to block 606 to determine TWOS morphology-based parameters whether or not the pattern-based TWOS is detected at block 604. In other words, the pattern-based parameter determination and pattern-based TWOS detection at blocks 602 and 604 and the morphology-based parameter determination and morphology-based TWOS detection at blocks 606 and 608 may both be performed, either sequentially or simultaneously, for every group of sensed events, to separately track the number of groups of consecutive sensed events that satisfy the pattern-based TWOS and the number of groups of sensed events that satisfy the morphology-based TWOS. In some instances, a group of sensed events may be counted by both counters if TWOS detection criteria are satisfied at both blocks 604 and 608.

While returning to block 114 is not explicitly shown in FIG. 14, after updating the TWOS counter(s) at block 612, it is to be understood that as long as the R-wave confirmation threshold is still being reached (and a tachyarrhythmia episode has not been detected), control circuit 80 may advance to the next group of consecutively sensed events at block 613 and return to block 602 to repeat the analysis of blocks 602 through 608. The next group of sensed events may be identified by moving one sensed event forward in time such that a moving group of six events (or other predetermined number of events) is analyzed for TWOS at blocks 602 through 608.

If the TWOS detection criteria are not satisfied at either of blocks 604 or 608, "no" branch of block 608, and the R-sense confirmation threshold is still being met, the next group of sensed events is identified at block 609 and evaluated for TWOS at blocks 602 through 608. This process performed at blocks 602 through 609 may be repeated for each moving group of consecutively sensed events as long as the R-sense confirmation threshold is still being met or until a VT or VF is detected.

In response to the NID being reached at block 132, based on RRIs determined from the cardiac electrical signal received via the first sensing vector 102, control circuit 80 determines if rejection criteria are satisfied at block 440. In the example of FIG. 14, TWOS rejection criteria are applied to the TWOS count (or counts when two counters are used) that is updated at block 612. At block 440, control circuit 80 may determine if TWOS rejection criteria are satisfied based on the TWOS count value. If TWOS has been detected a threshold number of times, the rejection criteria are satisfied at block 440. For example, if TWOS is detected at least three times based on the analysis of groups of sensed events, the rejection criteria are satisfied. The three TWOS detections may be pattern-based detections made at block 604, morphology-based detections made at block 608, or may include any combination of pattern-based detections and morphology-based detections.

In some examples, the TWOS rejection criteria may require that a threshold number of TWOS detections be made within a predetermined number of groups of R-wave sensed events. For example, if a TWOS count of at least three is reached within the last 20 groups of six consecutively sensed events, the rejection criteria are satisfied at block 440. The groups of sensed events may advance by one R-wave sensed event signal such that each group is overlapping with five of the R-wave sensed event signals of the neighboring groups of sensed events. In another example, if a count of at least three TWOS detections within the most recent 20 groups of consecutive R-wave sensed events and at least one of these TWOS detections is made within the most recent 10 groups of R-wave sensed events preceding the NID being reached, the TWOS rejection criteria are satisfied at block 440.

When two TWOS counters are used to individually track the number of groups of R-wave sensed events that satisfy the pattern-based TWOS criteria applied at block 604 and the number of groups of R-wave sensed events that satisfy the morphology-based TWOS criteria applied at block 608, both counters may be compared to respective TWOS rejection criteria thresholds at block 440. The respective TWOS rejection criteria thresholds applied to the values of the two separate counters may be the same or different. For example, a pattern-based TWOS count value that has reached X out of N groups of consecutive sensed events and a morphology-based TWOS count value that has reached Y out of the N groups of consecutive sensed events may satisfy the TWOS rejection criteria at block 440. In the example given above, N is 20 groups of six consecutive R-wave sensed events, and X and Y may be the same or different values, for example, X=3 and Y=2, or any other combination. In this way, the morphology-based and pattern-based TWOS criteria applied at block 604 and 608 may be performed concurrently with independent TWOS counters tracking the number of times TWOS criteria are satisfied for each. Both of the two TWOS counters are compared to respective rejection criteria thresholds at block 440. Alternatively or additionally, a sum of the two TWOS counters may be compared to a threshold value to determine if the rejection criteria are met at block 440.

If the NID is reached at block 132, but the rejection criteria are satisfied at block 440, the VT or VF detection is withheld at block 140. ATP or shock therapy is also withheld. If the rejection criteria are not satisfied, the VT or VF episode is detected at block 136 in response to the NID being reached at block 132. As described above in conjunction with FIG. 13, in some cases, VT and VF interval counters may track VT and VF intervals, respectfully, determined from the second sensing vector 104. An NID may be required to be reached by the VT and VF interval counters of the second sensing channel before determining if the rejection criteria are satisfied at block 440. The NID may be required to be reached after correcting any RRIs counted as a VT or VF interval that included an event classified as a T-wave.

Figure 15:
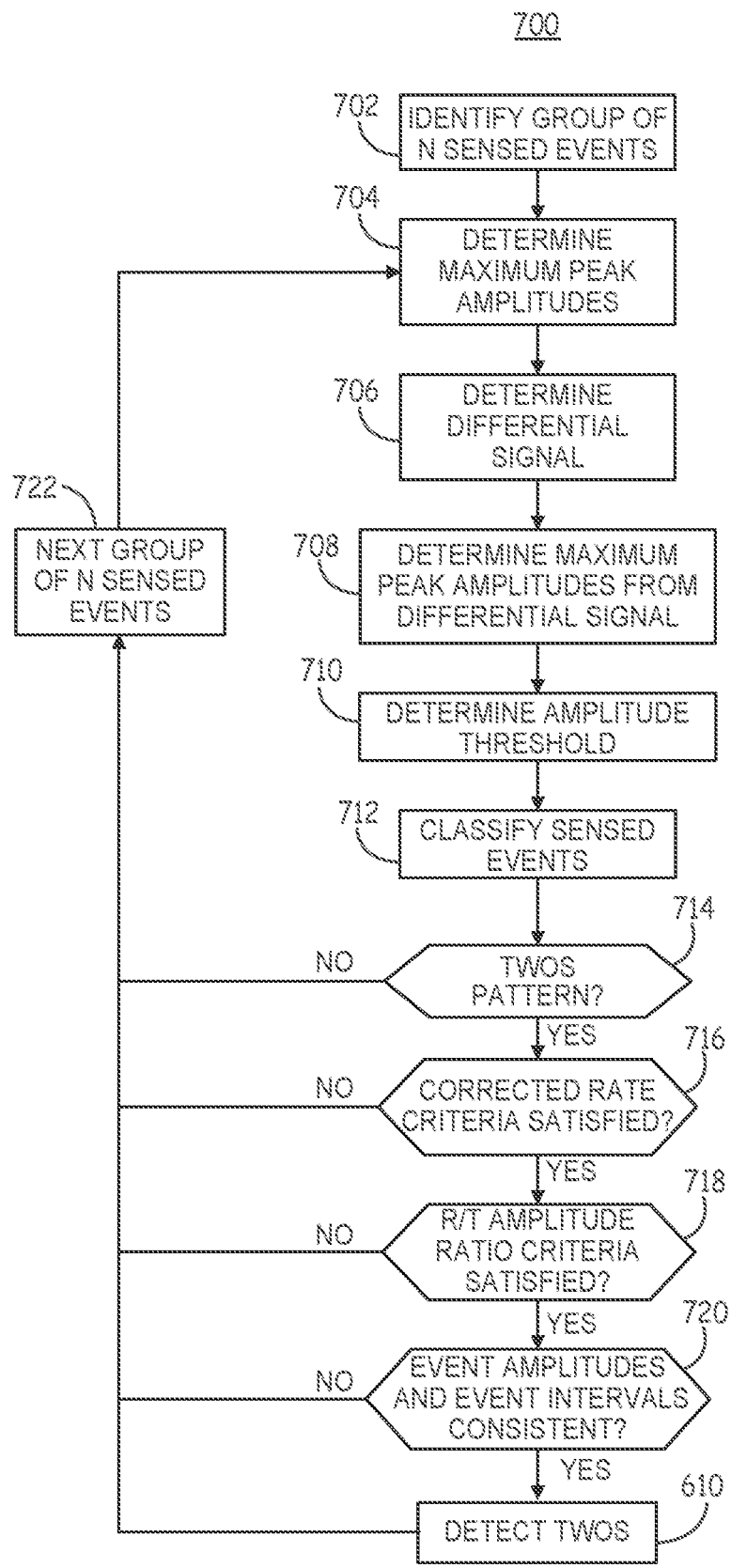
FIG. 15 is a flow chart of a method performed an ICD for determining TWOS pattern-based parameters and detecting pattern-based TWOS according to one example.

FIG. 15 is a flow chart 700 of a method performed by ICD 14 for determining TWOS pattern-based parameters and detecting TWOS according to one example. The method of flow chart 700 may correspond to the operations performed at blocks 602 and 604 of FIG. 14. At block 702, a group of n sensed events, e.g., six consecutively sensed events, is identified in response to the R-wave confirmation threshold being reached at block 114 of FIG. 14. The maximum peak amplitude of the rectified, first cardiac electrical signal (e.g., output of rectifier 65 shown in FIG. 5) for each of the n sensed events is determined at block 704. At block 706, a differential signal, for example a first order differential signal, is determined from the rectified, first cardiac electrical signal. The differential signal may correspond to the output 69 of differentiator 67 shown in FIG. 5). Control circuit 80 determines the maximum peak amplitude of the differential signal corresponding to each of the n sensed events at block 708.

The maximum peak amplitudes may be determined during a blanking period (e.g., 120 ms) following an R-wave sensed event signal or during a predefined window centered on the R-wave sensed event signal. The same timing window applied to obtain the maximum peak amplitude of the filtered, rectified first cardiac electrical signal at block 704 may be used to determine the maximum peak amplitudes of the differential signal for each sensed event at block 708.

At block 710, an amplitude threshold is determined from the maximum peak amplitudes of the differential signal. In one example, the group of n sensed events are evaluated in pairs of unique, consecutive events. For example, if six sensed events are identified at block 702, they may be labeled V1 through V6. The highest peak amplitude of each of the three pairs (V1 paired with V2, V3 paired with V4, and V5 paired with V6) is determined. If the six consecutive events represent an alternating pattern of R-waves and oversensed T-waves, the greater peak amplitude of the two paired events will represent a peak amplitude of an R-wave in an R-T (or T-R) pair. In other examples, the highest m peak amplitudes out of the n sensed events may be determined.

The maximum peak amplitudes of the differential signal may be averaged at block 710 to determine an average maximum peak amplitude. For example, the three greatest peak amplitudes of three pairs of events are averaged to determine the average maximum peak amplitude. An amplitude threshold may then be determined as a percentage of the average maximum peak amplitude. Other examples of determining an amplitude threshold from a differential signal are generally described in the above-incorporated U.S. Pat. No. 7,831,304 (Cao, et al.).

At block 712 each of the n sensed events of the group of sensed events are classified as either an R-wave or as a T-wave according to whether the differential signal crosses the amplitude threshold at a time corresponding to a respective R-wave sensed event signal. If the maximum peak amplitude of the differential signal for a given sensed event is less than the amplitude threshold, the sensed event is classified as a T-wave. Otherwise, the sensed event is classified as an R-wave.

At block 714, the classified events are analyzed by control circuit 80 to determine if a sensed event pattern that includes paired R-T events is present as evidence of TWOS. For example, a TWOS pattern may be identified at block 714 if a group of six sensed events includes three R-waves and three T-waves in an alternating pattern, or if the group of six sensed events includes four R-waves and two T-waves with each T-wave preceded by an R-wave. Other patterns or combinations of R-waves and T-waves would not be identified as a TWOS pattern in some implementations. If a TWOS pattern is not verified, the next group of n sensed events is identified at block 722, e.g., by advancing by one sensed event, and blocks 704 through 714 are repeated using the next sensed event and the preceding n−1 events, e.g., the preceding five sensed events in the example of a group of six sensed events.

If a TWOS pattern is detected at block 714 based on classified sensed events, additional TWOS detection criteria may be applied at blocks 716 through 720. For example, at block 716, the RRIs are determined between R-wave sensed event signals that correspond to sensed events that are classified as R-waves at block 712. These RRIs are "corrected" RRIs determined using only sensed events that are classified as R-waves based on the amplitude threshold determined at block 710. The corrected RRIs are compared to a minimum RRI of an upper heart rate limit and a maximum RRI of a lower heart rate limit. The upper and lower heart rate limits may define a range of heart rates that are considered true tachyarrhythmia rates. The maximum RRI may be a VT or VF interval threshold, e.g., the VF interval threshold, which may be 320 ms in some examples; a supraventricular tachycardia (SVT) interval limit, e.g., 240 ms to 320 ms; or a VT interval threshold which may be approximately 360 ms to about 500 ms when VT detection is enabled. If a predetermined number of the corrected RRIs fall outside the range defined by the upper and lower rate limits, ("no" branch of block 716) the next sensed event is obtained at block 722 and TWOS is not detected.

In some examples, a minimum RRI is not used and only a maximum RRI is applied to determine if corrected rate criteria are satisfied at block 716. If the predetermined number of corrected RRIs are greater than a TDI, an FDI, an SVT interval limit, or other maximum interval limit that defines the lower heart rate limit of the range of true tachyarrhythmia rates, the TWOS detection process may proceed to enable rejection of a VT or VF detection based on TWOS ("yes" branch of block 716). If a predetermined number of the corrected RRIs are not greater than the maximum interval limit, meaning that most or all of the corrected RRIs are still within a tachyarrhythmia interval range, rejection of an NID-based tachyarrhythmia due to detecting TWOS is not warranted ("no" branch of block 716). Control circuit 80 advances to block 722 to evaluate the next group of n sensed event.

If the rate criteria are satisfied at block 716, R/T amplitude ratio criteria are applied at block 718. The R/T ratio is the ratio of R-wave peak amplitudes and T-wave peak amplitudes determined for the classified sensed events. The R/T ratio may be determined from the filtered, rectified first cardiac electrical signal and/or from the differential signal based on the maximum peak amplitudes determined at block 704 and/or block 708, respectfully. A comparison of the R/T ratio from the filtered and rectified first cardiac electrical signal and the R/T ratio from the differential signal, referred to herein as R/T(DIFF) will indicate if the difference between the relative amplitudes of higher frequency R-waves and lower frequency T-waves has changed in the differential signal in a way that is consistent with the expected R-wave and T-wave frequency characteristics.

Generally, if the R/T ratio of the filtered, rectified first cardiac electrical signal is relatively small, the R/T ratio is expected to be less than a fraction of the R/T(DIFF) ratio because the differential signal is expected to enhance the amplitude difference between R-waves and T-waves. For example, in one embodiment, if the R/T ratio is less than 4 for the filtered, rectified first cardiac electrical signal, then the R/T ratio is expected to be less than approximately 75% of the R/T(DIFF) ratio.

If the R/T ratio of the filtered, rectified first cardiac electrical signal is relatively large, the R/T ratio may be larger than the R/T(DIFF) ratio, up to some percentage greater than the R/T(DIFF) ratio. In one embodiment, if the R/T ratio is greater than four, then the R/T ratio is expected to be less than approximately 125% of the R/T(DIFF) ratio. If the frequency response of the differential filtered first cardiac electrical signal is not consistent with a pattern of R-T sensing as verified by a comparison of the R/T ratio of the filtered and rectified first cardiac electrical signal and R/T(DIFF) at block 718, the next sensed event is obtained at block 722 ("no" branch of block 718). If the comparison of the R/T ratio to the R/T(DIFF) ratio meets criteria applied at block 718, this evidence supports a detection of TWOS. In this case, control circuit advances to block 720.

At block 720, the R-wave amplitudes, T-wave amplitudes, and R-T intervals are analyzed for consistency. This analysis may be performed using the filtered, rectified first cardiac electrical signal or the differential signal and the corresponding maximum peak amplitudes and R-T intervals determined for the sensed events classified as R-waves and T-waves at block 712. If the R-wave maximum peak amplitude, T-wave maximum peak amplitude and/or R-T interval criteria are not met at block 720, the next sensed event is obtained at block 722; TWOS is not detected for the current group of n-sensed events. A TWOS counter is not increased at block 612 of FIG. 14.

If all classified R-wave maximum peak amplitudes are similar, all classified T-wave maximum peak amplitudes are similar, and/or all R-T intervals are similar, TWOS is detected at block 610. All the criteria for verifying the presence of TWOS based on the classified sensed event pattern analysis have been satisfied. The last sensed event of the group of n sensed events that resulted in a TWOS detection may be labeled or flagged as TWOS. The TWOS count is increased by control circuit 80 at block 612 of FIG. 14 in response to the event pattern-based TWOS detection at block 610. As long as the R-wave confirmation threshold is still being reached (block 114 of FIG. 14), control circuit 80 advances to the next group of n sensed events at block 722 to repeat the pattern-based analysis of blocks 702 through 720.

Figure 16:
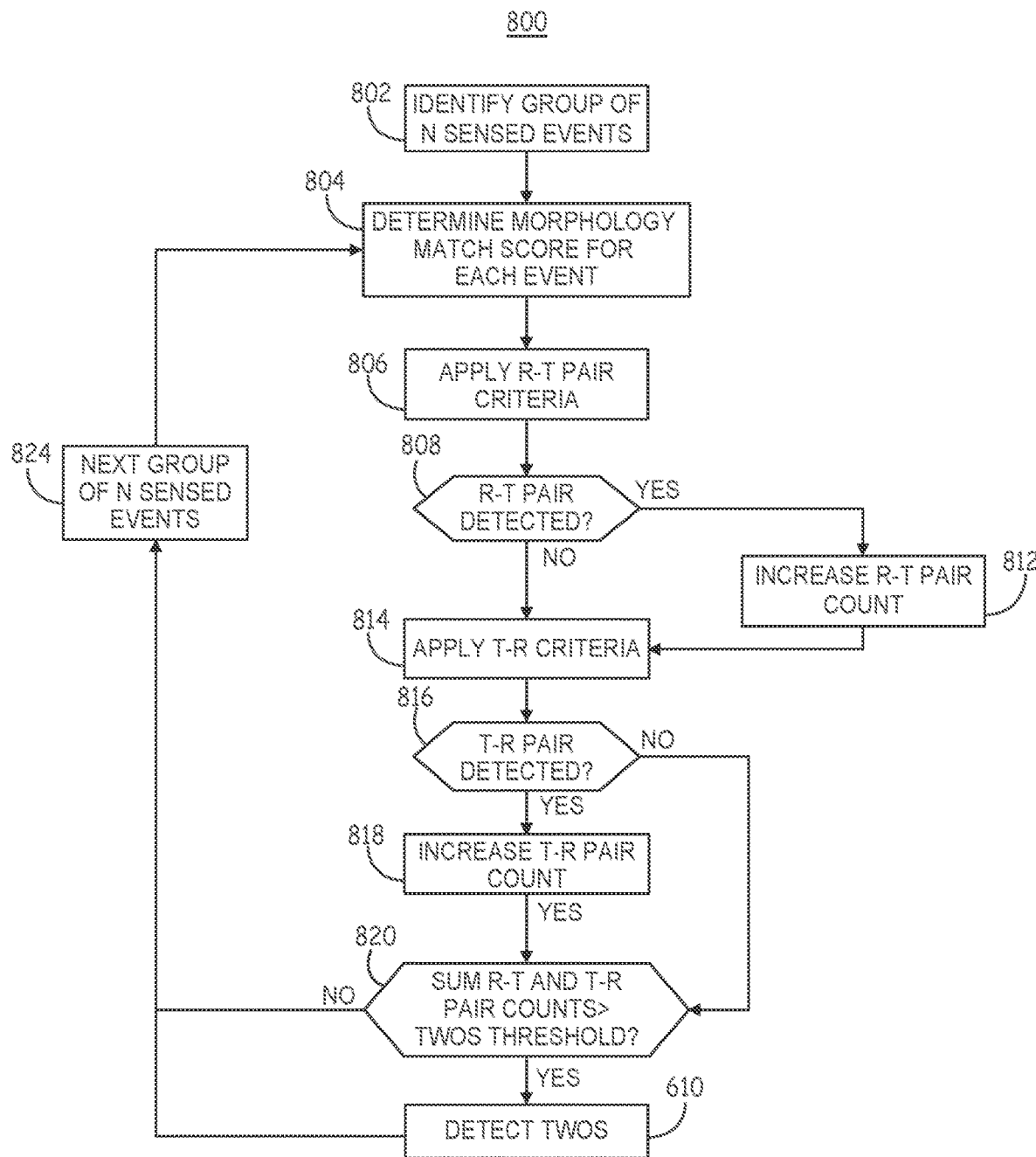
FIG. 16 is a flow chart of a method for morphology-based TWOS detection that may be performed by an ICD.

FIG. 16 is a flow chart 800 of a method for morphology-based TWOS detection that may be performed by control circuit 80 at blocks 606 and 608 of FIG. 14. The same group of n sensed events identified at block 702 of FIG. 15 for the event pattern-based TWOS detection method may be identified at block 802 of FIG. 16 for performing the morphology-based TWOS detection. The techniques of FIG. 15 and FIG. 16 may be performed simultaneously or sequentially on a group of n-sensed events. When two separate counters are used for tracking the number of the pattern-based TWOS detections and the number of morphology-based TWOS detections and rejection threshold criteria are applied to these separate counter values, false positive or false negative TWOS detections may be avoided when one of the TWOS detection methods is yielding false results. For example, if both counters are required to reach a respective TWOS threshold value, a false positive TWOS is avoided when only one counter reaches a TWOS detection threshold. If one counter is required to reach a TWOS threshold value in order to detect TWOS, a false negative is avoided when the other counter does not reach a TWOS threshold value.

In other examples, as shown in FIG. 14, the pattern-based analysis of classified sensed events may be performed first according to the techniques of FIG. 15 and if TWOS is not detected based on the pattern-based TWOS criteria, the morphology-based analysis of FIG. 16 may be performed on the same group of n sensed events. In this way, the morphology-based TWOS criteria enable control circuit 80 to still detect TWOS even when the pattern-based analysis results in a false negative TWOS detection.

At block 804, a morphology match score is determined for each second cardiac electrical signal segment stored for the group of n sensed events. The morphology match score may be determined by performing a wavelet transform analysis and comparing the wavelet transform of the notch-filtered, second cardiac electrical signal segment corresponding to each of the n sensed event signals to a previously determined normal R-wave template. Example methods for determining a morphology match score are generally disclosed in the above-incorporated U.S. Pat. No. 6,393,316 (Gillberg, et al.). While sensed event classifications made during the pattern-based TWOS detection method of FIG. 15 are based on comparing the differential signal of the first cardiac electrical signal to an amplitude threshold, for example in a sample-by-sample comparison to the amplitude threshold or by determining a maximum peak sample point amplitude of the differential signal and comparing the maximum peak amplitude the amplitude threshold, the morphology-based TWOS detection method of FIG. 16 analyzes the waveform morphology or shape of the second cardiac electrical signal over a predetermined number of sample points, e.g. over 200 to 500 ms, and compares the waveform morphology of the entire predetermined number of sample points to the same number of sample points of a normal R-wave template to obtain a morphology matching score. The morphology matching score represents how similar each sample point or group of sample points of the second cardiac electrical signal segment is to a corresponding sample point or group of sample points of the R-wave template.

R-T pair criteria are applied to the morphology match scores at block 806. In one example, two consecutive sensed events are determined to be an R-T pair if the morphology match score for the ith event is less than a maximum T-wave morphology threshold and the preceding (i−1) event has a morphology matching score that is greater than an R-wave matching threshold. For example, if the possible range of the morphology match score is 0 to 100, the R-wave matching threshold may be 60. A maximum T-wave threshold may be 20. As such, if the ith event has a morphology match score of 20 or less and the immediately preceding event has a morphology match score greater than 60, the two events satisfy the morphology-based R-T pair criteria at block 806.

The R-wave matching threshold used to identify R-T pairs at block 806 may be less than the match score threshold applied at block 432 of FIGS. 11 and 13 for determining if the beat morphology rejection rule is satisfied. A higher match score threshold may be used for confirming sensed R-waves based on beat morphology than the R-wave matching threshold used to distinguish R-waves from T-waves.

In other examples, the difference between the morphology match score for the ith event and the preceding (i−1) event may be determined at block 808 and required to be at least a predetermined threshold difference, e.g., a difference of at least 40 when the range of morphology match scores is from 0 to 100, to satisfy R-T pair criteria at block 814 (with the higher of the two morphology matching scores preceding the lower of the two morphology matching scores). In some instances, an R-wave morphology threshold and a maximum T-wave threshold defined based on the morphology match score of the i−1 event and a difference threshold may be used in combination to detect R-T pairs at block 808 (or T-R pairs at block 816 as described below) based on morphology matching scores. An R-wave morphology threshold may be required to be reached by the morphology matching score of the i−1 event. The maximum T-wave threshold is determined by control circuit 80 as the morphology match score of the i−1 event less a difference threshold. If the ith event has a morphology matching score that is at least the difference threshold less than the morphology match score of the i−1 event, an R-T pair is detected.

For example, if the i−1 event has a morphology matching score that is high, e.g., 90, exceeding a morphology matching score threshold of 60, for example, then a morphology matching score of the ith event that is at least a difference threshold less than the i−1 morphology matching score satisfies the R-T pair criteria applied at block 806. To illustrate, using a difference threshold of 40, if the morphology matching score for the notch-filtered, second cardiac electrical segment stored for the i−1 sensed event is 90, a morphology matching score of the ith sensed event that is 50 or less satisfies the R-T pair detection criteria.

In some examples, additional criteria may be applied to the two events at block 806 to confirm an R-T pair. For instance, the maximum peak amplitude of the differential signal for the ith sensed event (determined at block 708 of FIG. 15) may be required to be less than a predetermined percentage, e.g., 75%, of the differential signal maximum peak amplitude of the immediately preceding sensed event.

If the R-T pair criteria are satisfied at block 808, an R-T pair count is increased at block 812 for each pair of the group of n sensed events that satisfy the R-T pair criteria. In the case of a group of six sensed events identified at block 802, up to three R-T pairs may be detected resulting in a count value of up to three R-T pairs at block 812.

At block 814, T-R criteria may be applied to pairs of consecutive events included in the group of n sensed events. In some cases, the first event of the group of sensed event may be a T-wave resulting in a sequence of T-R pairs rather than R-T pairs. In some implementations, the group of six events may be evaluated in three pairs (events 1 and 2, events 3 and 4, and event 5 and 6) to identify each pair as an R-T pair, a T-R pair or neither. In other examples, the moving consecutive pairs (events 1-2, events 2-3, events 3-4, events 4-5 and event 5-6) may be evaluated for identifying R-T and T-R pairs at blocks 806 through 816.

In searching for T-R pairs, the morphology match score determined for the ith sensed event from the notch-filtered, second cardiac electrical signal is compared to the R-wave matching threshold and the immediately preceding (i−1) sensed event morphology match score is compared to the maximum T-wave threshold. If the morphology match score of the ith event is greater than the R-wave matching threshold and the immediately preceding morphology match score is less than the T-wave threshold (or a difference of the two scores reaches a threshold difference as described above with the i−1 score being lower than the ith score), a T-R pair is detected at block 816. In some examples, amplitude criteria may also be applied to detect the T-R pair. Continuing with the example given above, the maximum peak amplitude of the differential signal corresponding to the (i−1) sensed event may be required to be less than 75% of the maximum peak amplitude of the differential signal corresponding to the ith sensed event in order to detect a T-R pair. For each T-R pair detected in a group of n sensed events, the T-R pair count is increased by the control circuit 80 at block 818.

After increasing the T-R pair count for each T-R pair detected in the n sensed events, or if no T-R pairs are detected, "no" branch of block 816, the control circuit 80 determines the sum of the value of the R-T pair count and the value of the T-R pair count at block 820 and compares the sum to a TWOS threshold. While separate R-T and T-R pair counters are suggested by blocks 812 and 818, it is to be understood that a single counter of detected R-T and T-R pairs may be used to determine a summed count of R-T and T-R pairs that is compared to the TWOS threshold at block 820.

If a threshold number of R-T and/or T-R pairs is not counted control circuit 80 advances to the next group of n sensed events at block 824, as long as the R-sense confirmation threshold is still being reached at block 114 of FIG. 14. If a threshold number of R-T and/or T-R pairs are detected ("yes" branch of block 820), TWOS is detected at block 610, which corresponds to block 610 of FIG. 14. Each time the morphology based analysis results in a TWOS detection, the last event of the group of n sensed events may be labeled or flagged as TWOS. The TWOS count is increased at block 612 of FIG. 14 in response to a TWOS detection at block 610. As long as the R-sense confirmation threshold is still being reached at block 114 of FIG. 14, control circuit 80 advances to the next group of n sensed events at block 824.

As described above, if the NID is reached at block 132 of FIG. 14, control circuit 80 fetches the TWOS count value at block 440 to determine if the TWOS rejection criteria are satisfied at block 440. The TWOS count value may be a single value obtained from a TWOS counter that counts both morphology-based TWOS detections made according to the methods of FIG. 16 and the pattern-based TWOS detections made according to the methods of FIG. 15 or from two separate counters. When the TWOS rejection criteria are satisfied, a VT or VF detection is withheld and no therapy is delivered.

Thus, a method and apparatus for detecting TWOS and withholding a ventricular tachyarrhythmia episode detection in response to detecting TWOS in an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A medical device comprising:
 a sensing circuit configured to:
  sense a first cardiac electrical signal and a second cardiac electrical signal;
  produce an R-wave sensed event signal in response to the first cardiac electrical signal crossing an R-wave sensing threshold;
 a control circuit configured to:
  identify a first group of n R-wave sensed event signals produced by the sensing circuit;
  analyze the first cardiac electrical signal for determining if the first group of n R-wave sensed event signals meet first T-wave oversensing criteria;
  analyze at least the second cardiac electrical signal for determining if the first group of n R-wave sensed event signals meet second T-wave oversensing criteria;
  determine that at least one of the first T-wave oversensing criteria or the second T-wave oversensing criteria are met for the first group of n R-wave sensed event signals;
  detect T-wave oversensing in the first group of n R-wave sensed event signals in response to at least one of the first T-wave oversensing criteria being met or the second T-wave oversensing criteria being met for the first group of n R-wave sensed event signals;

determine that a threshold number of tachyarrhythmia detection intervals is reached for detecting a tachyarrhythmia based on the R-wave sensed event signals produced by the sensing circuit; and in response to detecting the T-wave oversensing in at least the group of n R-wave sensed event signals, withhold detecting the tachyarrhythmia when the threshold number of tachyarrhythmia detection intervals is reached.

2. The medical device of claim 1 wherein the control circuit is further configured to:

identify a plurality of groups of n R-wave sensed event signals produced by the sensing circuit, the plurality of groups of n R-wave sensed event signals including at least the first group of n R-wave sensed event signals;

for each respective group of n R-wave sensed event signals of the identified plurality of groups of n R-wave sensed event signals:

analyze the first cardiac electrical signal for determining if the respective group of n R-wave sensed event signals meets the first T-wave oversensing criteria;

analyze at least the second cardiac electrical signal for determining if the respective group of n R-wave sensed event signals meets second T-wave oversensing criteria;

detect T-wave oversensing in the respective group of n R-wave sensed event signals in response to at least one of the first T-wave oversensing criteria or the second T-wave oversensing being met;

determine that T-wave oversensing is detected in at least a first threshold number of the plurality of groups of n R-wave sensed event signals; and in response to at least detecting the T-wave oversensing in at least the first threshold number of the plurality of groups of n R-wave sensed event signals, withhold detecting the tachyarrhythmia when the threshold number of tachyarrhythmia detection intervals is reached.

3. The medical device of claim 2 wherein the control circuit is further configured to:

determine that T-wave oversensing is detected in at least a second threshold number of a most recent portion of the plurality of groups of n R-wave sensed event signals; and withhold detecting the tachyarrhythmia in response to determining that:

a) T-wave oversensing is detected in at least the first threshold number of the plurality of groups of n R-wave sensed event signals; and b) T-wave oversensing is detected in at least the second threshold number of the most recent portion of the plurality of groups of n R-wave sensed event signals.

4. The medical device of claim 2 wherein the plurality of groups of n R-wave sensed event signals comprise overlapping groups of n R-wave sensed event signals.

5. The medical device of claim 1 wherein the control circuit is further configured to:

identify a second group of n R-wave sensed event signals produced by the sensing circuit;

determine that the first T-wave oversensing criteria and the second T-wave sensing criteria are not met by the second group of n R-wave sensed event signals; and detect the tachyarrhythmia in response to at least the second group of n R-wave sensed event signals not meeting the first T-wave oversensing criteria and not meeting the second T-wave oversensing criteria; and the medical device further comprising a therapy delivery circuit configured to deliver an anti-tachyarrhythmia therapy in response to the control circuit detecting the tachyarrhythmia.

6. The medical device of claim 1 wherein the control circuit is further configured to analyze at least the second cardiac electrical signal for determining if the first group of n R-wave sensed event signals meet the second T-wave oversensing criteria by:

determining morphology matching scores from the second cardiac electrical signal for the first group of n R-wave sensed event signals;

determining maximum peak amplitudes from the first cardiac electrical signal for the first group of n R-wave sensed event signals; and determining if the first group of n R-wave sensed event signals meet the second T-wave oversensing criteria based on the morphology match scores and the maximum peak amplitudes.

7. The medical device of claim 1 wherein the control circuit is further configured to analyze at least the second cardiac electrical signal for determining if the first group of n R-wave sensed event signals meet the second T-wave oversensing criteria by:

determining a morphology match score from the second cardiac signal for each R-wave sensed event signal of the first group of n R-wave sensed event signals;

detect at least one R-wave and T-wave pair based on the morphology match scores; and determine that the second T-wave oversensing criteria are met based on detecting the at least one R-wave and T-wave pair.

8. The medical device of claim 7 wherein the control circuit is further configured to:

compare a first morphology match score of the determined morphology match scores to a first morphology match threshold;

compare a second morphology match score of the determined morphology match scores to a second morphology match threshold different than the first morphology match threshold; and detect the at least one R-wave and T-wave pair based on at least the first morphology match score being greater than the first morphology match threshold and the second morphology match score being less than the second morphology match threshold.

9. The medical device of claim 8 wherein the control circuit is further configured to:

determine a differential signal from the first cardiac electrical signal; and detect the at least one R-wave and T-wave pair when a first amplitude of the differential signal associated with the R-wave and T-wave pair is less than a threshold percentage of a second amplitude of the differential signal associated with the R-wave and T-wave pair.

10. The medical device of claim 1 wherein the control circuit is further configured to analyze the first cardiac electrical signal for determining if the group of n R-wave sensed event signals meet first T-wave oversensing criteria by:

identifying a highest peak amplitude from each of multiple pairs of the first group of n R-wave sensed event signals;

determining an amplitude threshold from the identified highest peak amplitudes;

classifying each R-wave sensed event signal of the group of n R-wave sensed event signals as either an R-wave or a T-wave based on whether the first cardiac electrical signal crosses the determined amplitude threshold at a time corresponding to a respective R-wave sensed event signal of the group of n R-wave sensed event signals;

determining that at least a threshold number of the classified R-wave sensed event signals are classified as T-waves; and determining that the R-wave sensed event signals that are classified as T-waves alternate with R-wave sensed event signals that are classified as R-waves.

11. The medical device of claim 1 further comprising a therapy delivery circuit configured to deliver an anti-tachyarrhythmia therapy in response to the control circuit detecting tachyarrhythmia.

12. A method comprising:

sensing a first cardiac electrical signal and a second cardiac electrical signal;

producing an R-wave sensed event signal in response to the first cardiac electrical signal crossing an R-wave sensing threshold;

identifying a first group of n R-wave sensed event signals produced by the sensing circuit;

analyzing the first cardiac electrical signal for determining if the first group of n R-wave sensed event signals meet first T-wave oversensing criteria;

analyzing at least the second cardiac electrical signal for determining if the first group of n R-wave sensed event signals meets second T-wave oversensing criteria;

determining whether at least one of the first T-wave oversensing criteria or the second T-wave oversensing criteria are met for the first group of n R-wave sensed event signals;

determining that a threshold number of tachyarrhythmia detection intervals is reached for detecting a tachyarrhythmia based on the R-wave sensed event signals produced by the sensing circuit;

withholding detecting the tachyarrhythmia when the threshold number of tachyarrhythmia detection intervals is reached and at least one of the first T-wave oversensing criteria or the second T-wave oversensing criteria are determined to be met for at least the first group of n R-wave sensed event signals;

detecting the tachyarrhythmia when the threshold number of tachyarrhythmia detection intervals is reached and neither the first T-wave oversensing criteria or the second T-wave oversensing criteria are determined to be met for the first group of n R-wave sensed event signals; and delivering an anti-tachyarrhythmia therapy in response to detecting tachyarrhythmia.

13. The method of claim 12 further comprising:

identifying a plurality of groups of n R-wave sensed event signals produced by the sensing circuit, the plurality of groups of n R-wave sensed event signals including at least the first group of n R-wave sensed event signals;

for each respective group of n R-wave sensed event signals of the identified plurality of groups of n R-wave sensed event signals:

analyzing the first cardiac electrical signal for determining if the respective group of n R-wave sensed event signals meets the first T-wave oversensing criteria;

analyzing at least the second cardiac electrical signal for determining if the respective group of n R-wave sensed event signals meets second T-wave oversensing criteria;

detecting T-wave oversensing in the respective group of n R-wave sensed event signals in response to at least one of the first T-wave oversensing criteria or the second T-wave oversensing being met;

determining that T-wave oversensing is detected in at least a first threshold number of the plurality of groups of n R-wave sensed event signals; and withholding detecting the tachyarrhythmia when the threshold number of tachyarrhythmia detection intervals is reached and T-wave oversensing is detected in at least the first threshold number of the plurality of groups of n R-wave sensed event signals.

14. The method of claim 13 further comprising:

determining that T-wave oversensing is detected in at least a second threshold number of a most recent portion of the plurality of groups of n R-wave sensed event signals; and withholding detecting the tachyarrhythmia in response to determining that:

a) T-wave oversensing is detected in at least the first threshold number of the plurality of groups of n R-wave sensed event signals; and b) T-wave oversensing is detected in at least the second threshold number of the most recent portion of the plurality of groups of n R-wave sensed event signals.

15. The method of claim 13 wherein the plurality of groups of n R-wave sensed event signals comprise overlapping groups of n R-wave sensed event signals.

16. The method of claim 12 further comprising, when detecting the tachyarrhythmia is withheld:

identifying a second group of n R-wave sensed event signals produced by the sensing circuit;

determining that the first T-wave oversensing criteria and the second T-wave sensing criteria are not met by the second group of n R-wave sensed event signals; and detecting the tachyarrhythmia in response to at least the second group of n R-wave sensed event signals not meeting the first T-wave oversensing criteria and not meeting the second T-wave oversensing criteria.

17. The method of claim 12 wherein analyzing at least the second cardiac electrical signal for determining if the first group of n R-wave sensed event signals meet the second T-wave oversensing criteria comprises:

determining morphology match scores from the second cardiac electrical signal for the first group of n R-wave sensed event signals;

determining maximum peak amplitudes from the first cardiac electrical signal for the first group of n R-wave sensed event signals; and determining if the first group of n R-wave sensed event signals meet the second T-wave oversensing criteria based on the morphology match scores and the maximum peak amplitudes.

18. The method of claim 12 wherein analyzing at least the second cardiac electrical signal for determining if the first group of n R-wave sensed event signals meet the second T-wave oversensing criteria comprises:

determining a morphology match score from the second cardiac signal for each R-wave sensed event signal of the first group of n R-wave sensed event signals;

detecting at least one R-wave and T-wave pair based on the morphology match scores; and determine that the second T-wave oversensing criteria are met based on detecting the at least one R-wave and T-wave pair.

19. The method of claim 18 further comprising:
comparing a first morphology match score of the determined morphology match scores to a first morphology match threshold;
comparing a second morphology match score of the determined morphology match scores to a second morphology match threshold different than the first morphology match threshold; and
detecting the at least one R-wave and T-wave pair based on at least the first morphology match score being greater than the first morphology match threshold and the second morphology match score being less than the second morphology match threshold.

20. The method of claim 19 further comprising:
determining a differential signal from the first cardiac electrical signal; and
detecting the at least one R-wave and T-wave pair when a first amplitude of the differential signal associated with the R-wave and T-wave pair is less than a threshold percentage of a second amplitude of the differential signal associated with the R-wave and T-wave pair.

21. The method of claim 12 wherein analyzing the first cardiac electrical signal for determining if the group of n R-wave sensed event signals meet first T-wave oversensing criteria comprises:
identifying a highest peak amplitude from each of multiple pairs of the first group of n R-wave sensed event signals;
determining an amplitude threshold from the identified highest peak amplitudes;
classifying each R-wave sensed event signal of the group of n R-wave sensed event signals as either an R-wave or a T-wave based on whether the first cardiac electrical signal crosses the determined amplitude threshold at a time corresponding to a respective R-wave sensed event signal of the group of n R-wave sensed event signals;
determining that at least a threshold number of the classified R-wave sensed event signals are classified as T-waves; and
determining that the R-wave sensed event signals that are classified as T-waves alternate with R-wave sensed event signals that are classified as R-waves.

22. A non-transitory, computer-readable storage medium comprising a set of instructions which, when executed by a control circuit of a medical device, cause the device to:
sense a first cardiac electrical signal and a second cardiac electrical signal;
produce an R-wave sensed event signal in response to the first cardiac electrical signal crossing an R-wave sensing threshold;
identify a group of n R-wave sensed event signals produced by the sensing circuit;
analyze the first cardiac electrical signal for determining if the group of n R-wave sensed event signals meet first T-wave oversensing criteria;
analyze at least the second cardiac electrical signal for determining if the group of n R-wave sensed event signals meet second T-wave oversensing criteria;
determine whether T-wave oversensing is detected in the group of n R-wave sensed event signals based on whether at least one of the first T-wave oversensing criteria is met or the second T-wave oversensing criteria is met for the group of n R-wave sensed event signals;
determine that a threshold number of tachyarrhythmia detection intervals is reached for detecting a tachyarrhythmia based on the R-wave sensed event signals produced by the sensing circuit;
withhold detecting the tachyarrhythmia when the threshold number of tachyarrhythmia detection intervals is reached and T-wave oversensing is detected; and
deliver an anti-tachyarrhythmia therapy when the threshold number of tachyarrhythmia detection intervals is reached and T-wave oversensing is not detected.

\* \* \* \* \*